(12) United States Patent
Davies et al.

(10) Patent No.: US 11,419,676 B2
(45) Date of Patent: Aug. 23, 2022

(54) MEDICAL DEVICE HAVING A SUPPORT STRUCTURE

(71) Applicant: Baylis Medical Company Inc., Montreal (CA)

(72) Inventors: Gareth Davies, Toronto (CA); John Paul Urbanski, Toronto (CA); Rund Abou-Marie, Mississauge (CA)

(73) Assignee: Boston Scientific Medical Device Limited, Galway (IE)

( * ) Notice: Subject to any disclaimer, the term of this patent is extended or adjusted under 35 U.S.C. 154(b) by 272 days.

(21) Appl. No.: 16/381,102

(22) Filed: Apr. 11, 2019

(65) Prior Publication Data

US 2019/0231424 A1    Aug. 1, 2019

Related U.S. Application Data

(63) Continuation of application No. 14/851,412, filed on Sep. 11, 2015, now Pat. No. 10,792,096, which is a
(Continued)

(51) Int. Cl.
*A61B 18/14*    (2006.01)
*A61B 5/00*    (2006.01)
(Continued)

(52) U.S. Cl.
CPC ........ *A61B 18/1492* (2013.01); *A61B 5/0215* (2013.01); *A61B 5/6852* (2013.01); *A61N 1/056* (2013.01); *A61B 2018/00101* (2013.01); *A61B 2018/00351* (2013.01); *A61B 2090/3966* (2016.02); *A61B 2218/002* (2013.01); *A61M 25/0041* (2013.01); *A61M 25/0054* (2013.01);
(Continued)

(58) Field of Classification Search
CPC ...... A61B 2090/3966; A61B 2218/002; A61B 17/3476; A61B 17/3478; A61B 18/1477; A61B 2017/00247; A61B 2017/00862; A61B 2017/00867; A61B 2018/00083; A61B 2018/00136; A61B 2018/00297; A61B 2018/00351; A61B 2018/00357; A61B 2018/00375; A61B 2018/00404; A61B 2090/064; A61B 2090/0811; A61B 2090/3983; A61B 2218/007; A61B 5/0215; A61B 5/6848; A61B 6/12; A61B 90/02

See application file for complete search history.

(56) References Cited

U.S. PATENT DOCUMENTS

| | | | | |
|---|---|---|---|---|
| 6,099,524 A | * | 8/2000 | Lipson | A61B 5/287 606/41 |
| 2008/0086120 A1 | * | 4/2008 | Mirza | A61B 18/1482 606/41 |
| 2015/0231367 A1 | * | 8/2015 | Salstrom | A61M 25/0138 604/95.01 |

* cited by examiner

*Primary Examiner* — Tigist S Demie
(74) *Attorney, Agent, or Firm* — Dennis Haszko

(57) ABSTRACT

Embodiments of medical devices and methods are disclosed. The medical devices typically comprises an elongate member with a proximal region and a distal region. The distal region comprises a flexible portion that is more flexible than the proximal region of the medical device. The flexible region includes gaps in the sidewall of the elongate member. Furthermore, the medical device comprises a rigid energy delivery device at the distal end which is configured to deliver energy to tissue when energy is supplied to the energy delivery device. In some embodiments, the medical device comprises a support spine configured to provide support to the flexible portion of the elongate member.

15 Claims, 17 Drawing Sheets

Related U.S. Application Data continuation-in-part of application No. PCT/IB2014/059696, filed on Mar. 12, 2014.

(60) Provisional application No. 61/777,368, filed on Mar. 12, 2013, provisional application No. 61/781,231, filed on Mar. 14, 2013.

(51) Int. Cl.
*A61B 5/0215* (2006.01)
*A61N 1/05* (2006.01)
A61B 90/00 (2016.01)
A61M 25/00 (2006.01)
A61B 18/00 (2006.01)
A61M 25/09 (2006.01)

(52) U.S. Cl.
CPC .............. *A61M 2025/0003* (2013.01); *A61M 2025/09133* (2013.01)

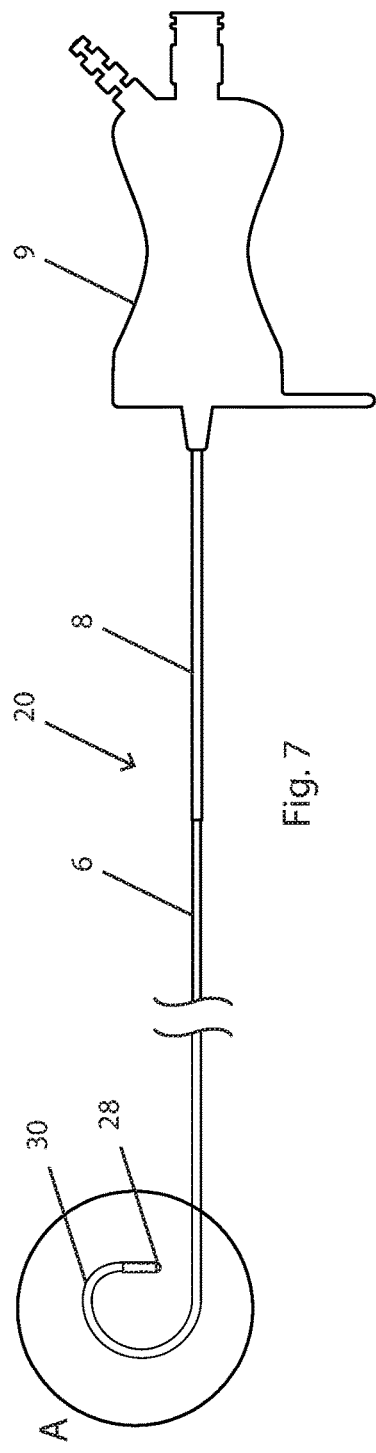
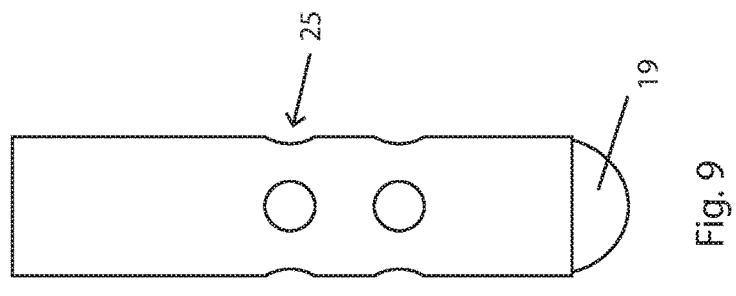
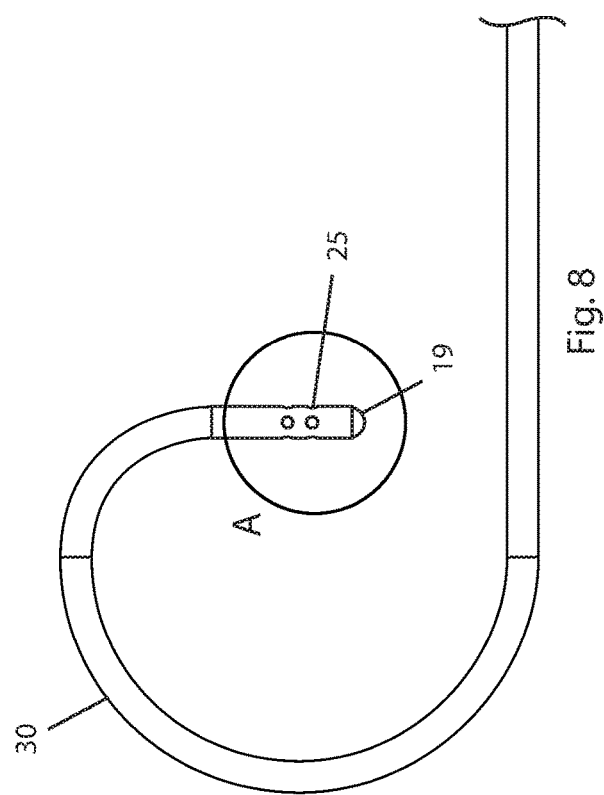
Fig. 7
Fig. 9
Fig. 8

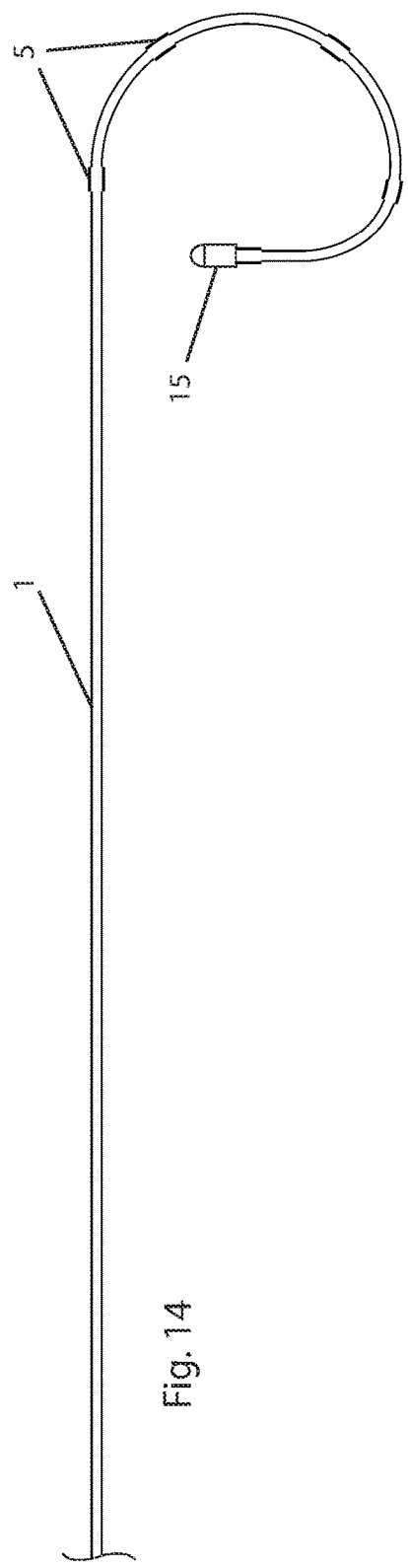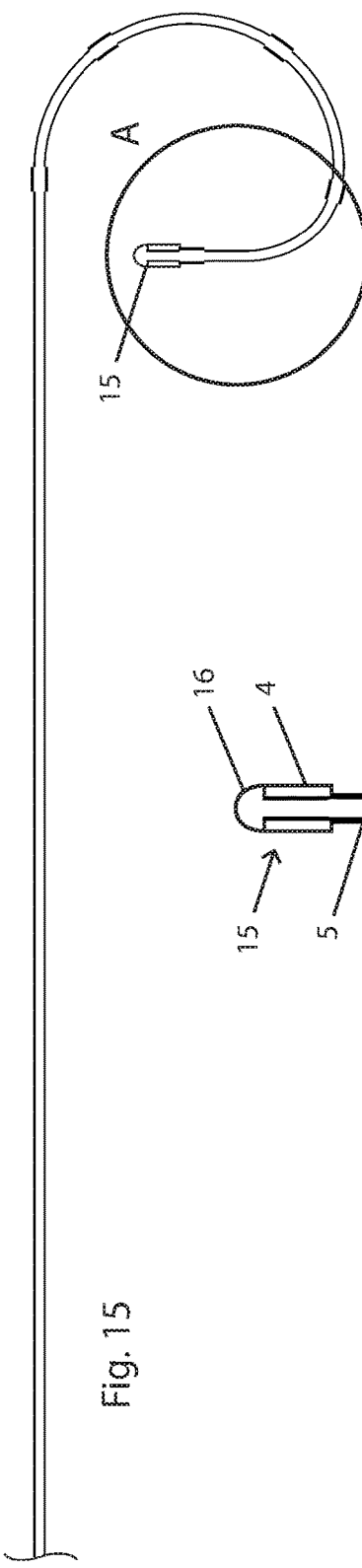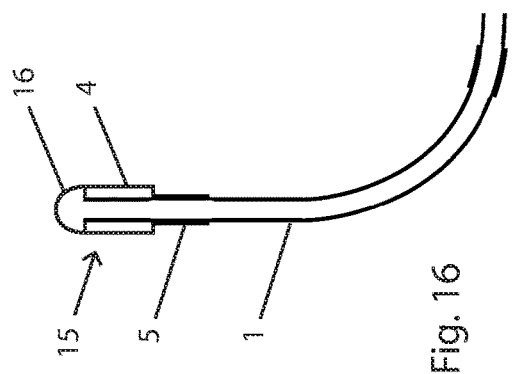

MEDICAL DEVICE HAVING A SUPPORT STRUCTURE

TECHNICAL FIELD

The disclosure relates to a medical device. More specifically, it relates to an elongate medical device with a support spine.

SUMMARY OF THE DISCLOSURE

Embodiments of the present invention include a medical device comprising a flexible elongate member that defines a lumen, and a support spine affixed to the distal end and extending proximally therefrom within the elongate member lumen. In typical embodiments, the support spine is not attached to a lumen surface or embedded in the elongate member's sidewall. In some embodiments, the support wire is configured to support at least a portion of the elongate member. Some embodiments of the medical device provide for distal end fluid delivery by defining apertures at or near the distal end that enable fluid communication between the lumen and the outside environment. Furthermore, in some such embodiments, the support spine extends from the distal end within a distal portion of the lumen such that a proximal portion of the lumen is substantially unobstructed by the support spine, thereby minimizing effects on fluid flow, at least within the proximal portion of the lumen.

In a first broad aspect, embodiments of the present invention include a medical device comprising a flexible elongate member configured for traversing body lumens, the elongate member defining a lumen in fluid communication with at least one distal aperture; and a support spine within the lumen extending proximally from the distal end of the medical device within a distal portion of the lumen; and terminating within a distal portion of the lumen. In some embodiments, the elongate member is generally tubular in configuration, a distal portion of its sidewall has cuts therein to increase flexibility, and the support wire minimizes the bending stress on any one cut by supporting the wall of the elongate member and distributing the bending stress along the elongate member i.e. the spine can act as a bridge across the cuts to distribute the bending stress along the elongate member.

As a further feature of the first broad aspect, in some embodiments, the medical device further comprises an energy delivery device at the distal end of the elongate member operable to be electrically coupled to an energy source. In some such embodiments, energy can flow through the wall of the elongate member to the energy delivery device, leaving the lumen sufficiently open for functioning as a conduit for fluid flow. In certain embodiments, the wall is comprised of an electrically conductive material and the energy is electrical energy, for example, in the radiofrequency range.

In a second broad aspect, embodiments of the present invention include a medical device comprising an elongate member defining a lumen and configured for traversing body lumens; and a support spine coupled at its distal end to a distal end of the medical device, extending proximally therefrom to its proximal end that is not coupled to the elongate member. The support spine is configured to support a tensile side of the elongate member during bending. In some embodiments, the elongate member is generally tubular in configuration and a distal portion of its sidewall has cuts therein to increase flexibility. The cuts may be partially or completely through the sidewall. The support wire minimizes the bending stress on any one cut by supporting the wall of the elongate member to distribute the bending stress along the length of the elongate member.

As a feature of the second broad aspect, in some embodiments of the medical device, the lumen is in fluid communication with at least one aperture at or near a distal end of the elongate member.

As another feature of the second broad aspect, in some embodiments of the medical device, an energy delivery device at the distal end of the elongate member is operable to be in communication with an energy source. In certain embodiments, energy flows through the wall of the elongate member, whereby the lumen is left sufficiently open to function as a conduit for fluid flow. In certain embodiments, the wall is comprised of an electrically conductive material and the energy is electrical energy.

As another feature of the second broad aspect, in some embodiments of the medical device, the support wire/spine has shape memory.

As a further feature of the second broad aspect, in some embodiments of the medical device, a portion of the elongate member defines a curve. Alternative embodiments of the second broad aspect include the elongate member being substantially straight (i.e. not having a substantially curved portion).

In accordance with a third broad aspect of the invention, a method of surgery is described. In some embodiments, the method comprises (i) introducing a medical device into a body of a patient, the medical device comprising an elongate member having a distal region and a proximal region, an energy delivery device proximate to the distal region capable of cutting material, and a lumen and apertures operable to communicate with a pressure sensing mechanism for determining pressure in the body proximate to the distal region; (ii) positioning the energy delivery device at a first desired location in the patients body substantially adjacent material to be cut; (iii) delivering energy using the energy delivery device to cut said material; and (iv) measuring pressure in the body using the pressure sensing mechanism in order to determine the position of the medical device before and/or after step (iii). In some embodiments of this aspect, step (ii) comprises delivering fluid for imaging at the first desired location in the patients body.

Some embodiments of the method further comprise a step (v) of advancing the device to a second desired location. In certain embodiments of this aspect, the medical device comprises at least one radiopaque marker and step (v) comprises monitoring at least one of the radiopaque markers before, during, or after advancement. Some embodiments of the method comprise a further step (vi) of measuring pressure at the second location to confirm the position of the medical device at the second location. In certain embodiments, the medical device comprises at least one radiopaque marker, and step (vi) is performed after confirming the position of at least a portion of the pressure sensing mechanism (e.g. an aperture of the medical device) at the second location using the radiopaque markers.

In some embodiments of this method aspect, step (i) comprises introducing the device into the patient's vasculature and/or other body lumens. The step of introducing the device into the patient's vasculature typically comprises inserting the device into a dilator and a guiding sheath positioned in the patients vasculature. In certain embodiments, the device and at least one of the dilator and sheath comprise a radiopaque marker, and step (ii) comprises aligning the radiopaque markers of the devices to aid in positioning the devices. For certain alternative embodiments of the method, step (v) comprises advancing the dilator and the sheath into the second location together over the spatially fixed medical device. In other alternative embodiments, step (v) comprises advancing the dilator, sheath, and medical device all together into the second location.

In accordance with the method aspect of the present invention, in certain embodiments, the material to be cut is tissue located on an atrial septum of a heart. In some embodiments, the region of tissue is the fossa ovalis of a heart. In such embodiments, the pressure measured at the second location is the blood pressure in the left atrium of the heart.

In some alternative embodiments, the method further includes delivering contrast fluid visible using an imaging system in order to confirm the position of the medical device at the second desired location.

Certain embodiments of the method include the elongate member having a distal region capable of adopting a curved shape. In some such embodiments, after the medical device tip advances through a material or out the end of the dilator, the pre-shaped support spine biases the distal region to adopt a curved shape that directs the functional tip in a desired direction. In some embodiments, the curved shape is defined by a radial arc and the functional tip is directed away from cardiac structures to decrease the risk of unwanted injury. As an example, the distal region is configured to form a 270 degree curve.

BRIEF DESCRIPTION OF THE DRAWINGS

In order that the invention may be readily understood, embodiments of the invention are illustrated by way of examples in the accompanying drawings, in which:

FIG. 7 is an illustration of an embodiment of a medical device with a curved end portion and a handle;

FIG. 8 is an illustration of detail A of FIG. 7;

FIG. 9 is an illustration of detail A of FIG. 8;

FIG. 14 is an illustration of the installed configuration of the core or support spine assembly of the embodiment of FIG. 10;

FIG. 15 is a cut-away view of the embodiment of FIG. 14;

FIG. 16 is an illustration of detail A of FIG. 15;

DETAILED DESCRIPTION

The present inventors have conceived and reduced to practice a novel and inventive medical device for creating punctures or perforations in tissues. Embodiments of the medical device include features allowing for transfer of fluids through the device, while providing for internal support of the device, particularly when the device is bent or curved.

In typical embodiments of medical device 20, support spine 1 is connected to other features of device 20 at the distal end of the medical device, and the proximal end of support spine 1 remains un-attached to, and independent of, elongate member 6 and any other part of medical device 20. In other words, substantially only the distal end of support spine 1 is attached or otherwise connected to the medical device 20. This configuration allows the proximal end of support spine 1 to move longitudinally and laterally relative to the inner wall of the elongate member (e.g. a hypotube), which allows the distal end of medical device 20 (where the support spine 1 and elongate member 6 are joined) to bend or curve unimpeded by support spine 1. The ability of the distal end portion of medical device 20 to bend or curve facilitates advancement of the device through tortuous vasculature and other body vessels.

Furthermore, the proximal end of support spine 1 is unattached to medical device 20 so that it does not constrain the curvature of the device. Elongate member 6 and support spine 1 have different bend radii as a result of differences in the bend axis due to the wall thickness of the elongate member 6 and the position of the support spine 1. When the medical device 20 is bent about its distal portion, the difference in bend radius results in different arc lengths for elongate member 6 and support spine 1. If the proximal end of support spine 1 was fixed at a proximal portion of medical device 20, the relative arc-lengths of elongate member 6 and support spine 1 would be fixed, and the catheter curvature would be constrained by support spine 1.

Figure 25A:
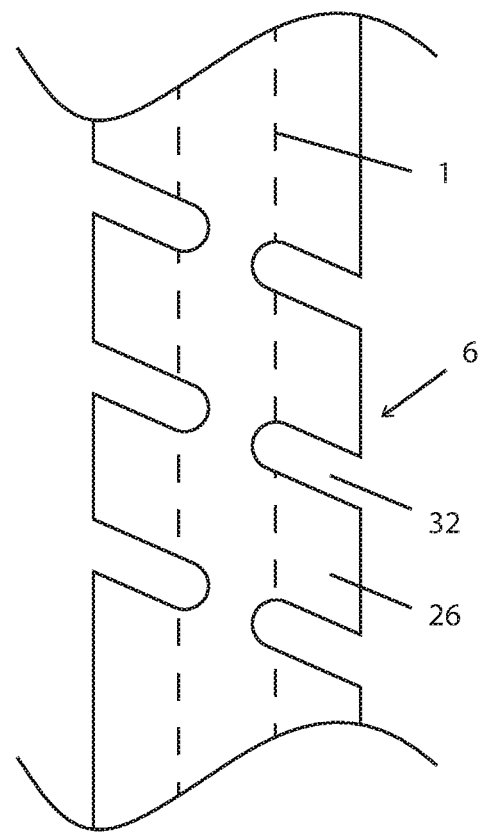
FIGS. 25A and 25B are diagrams of a portion of an elongate member embodiment with a discontinuous spiral cut therein and a support wire.
Figure 25B:
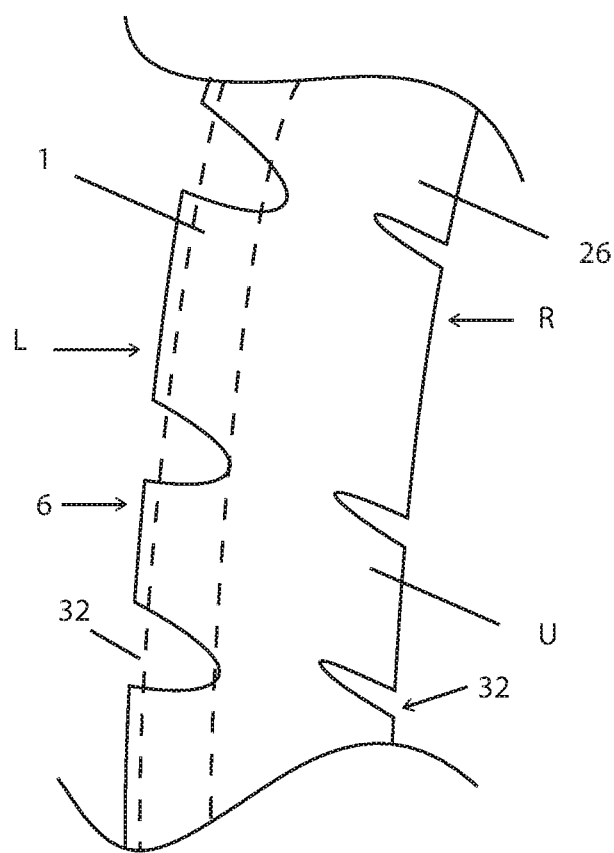

Typical embodiments of medical device 20 have cuts 32 into the sidewall of elongate member 6 to increase flexibility (as shown in FIGS. 25A and 25B). Such cuts have the drawback of reducing the strength of a tubular structure and increasing the chances of the device breaking. When elongate member 6 bends during advancement through tortuous body lumens, support spine 1 rests against the tensile side of elongate member 6 and provides support for elongate member 6 (as shown in FIG. 25B). By providing support to the tensile side, the support spine distributes the stress of the bend or curve along a longer length of elongate member 6 than in the case of an unsupported elongate member (i.e. an elongate member that does not have a spine). Consequently, the stress of the bend is spread amongst more cuts 32 and uncut portions (U) of the sidewall, resulting in reduced risk of damage to the elongate member (e.g. breaking at one isolated cut) by the stress forces of the bend or curve. Thus, the support spine, as shown in FIG. 25B, assists in distributing the load along elongate member 6. Furthermore, since an applied load also deflects the support spine, the support spine takes some of the load directly.

Also, support spine 1 allows elongate member 6 to have a smoother curve than is provided by an unsupported elongate member as the support spine functions as a spline (i.e. a supporting strip of material). Inclusion of support spine 1 reduces the frequency of abrupt bends along elongate member 6.

Some embodiments of medical device 20 include support spine 1 being comprised of a material with shape memory, such as nitinol, whereby the device can be designed and manufactured to be biased towards a pre-configured shape, for example, curved or straight.

Figure 26:
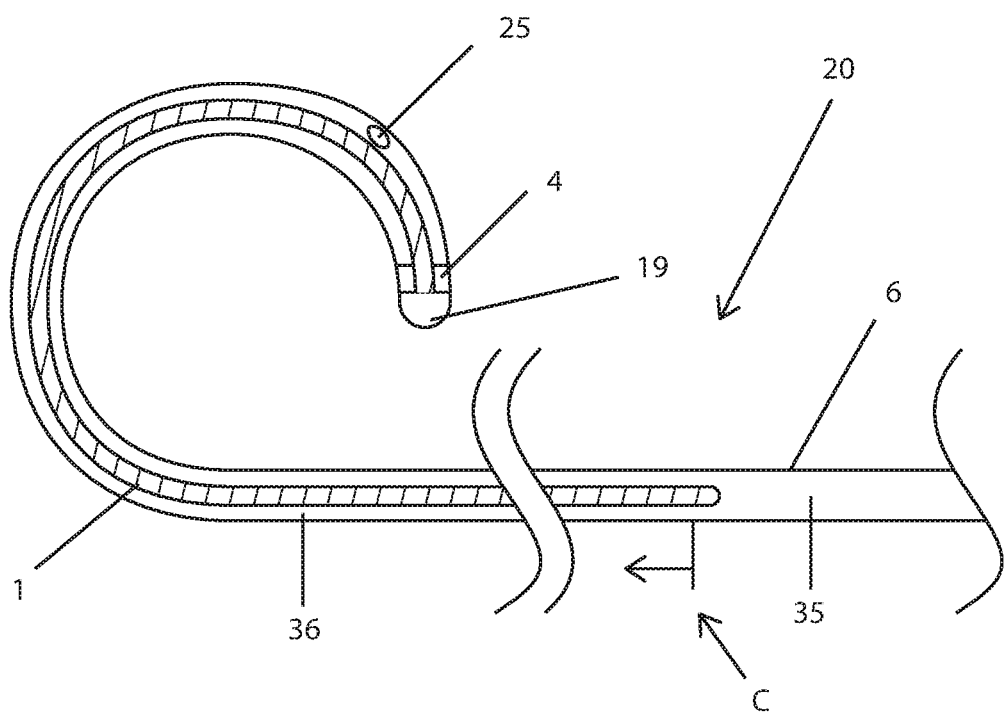
FIG. 26 is a diagram showing a lumen distal portion containing a support spine and a proximal lumen portion that lacks the support spine.

As shown in FIG. 26, typical embodiments of medical device 20 include a support spine 1 affixed to the distal end of medical device 20 inside lumen 26 and extending proximally within the lumen, and an aperture 25 for fluid delivery at the distal end of medical device 20. (Alternative embodiments do not have an aperture 25). For typical embodiments, the support spine 1 extends from the distal end within lumen distal portion 36 such that a lumen proximal portion 35 is substantially unobstructed by the support spine, thereby minimizing effects on fluid flow.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

A medical device as described herein comprises a flexible elongate member that defines a lumen, and an independent support spine affixed to the distal end and extending proximally therefrom within the elongate member lumen whereby the support spine can support the elongate member. The spine is not attached to a lumen surface or embedded in the elongate member's sidewall. Some embodiments of the medical device further provide for fluid delivery at the distal end through apertures defined by the flexible elongate member that enable fluid communication between the lumen and the outside environment. In some such embodiments, the support spine extends proximally from the distal end within a distal portion of the lumen such that a proximal portion of the lumen is substantially unobstructed by the support spine, thereby minimizing effects on fluid flow within the proximal portion of the lumen.

While some embodiments of the medical device have distal end apertures, alternative embodiments do not. Furthermore, while some embodiments of the medical device have distal end energy delivery means, alternative embodiments do not. For example, some embodiments include a sensor for gathering sensory input, such as probes having temperature sensors and/or impedance sensors. In some such embodiments, the probes have an elongate member comprised of electrically conductive material(s) and/or electrically non-conductive material(s).

Figure 1:
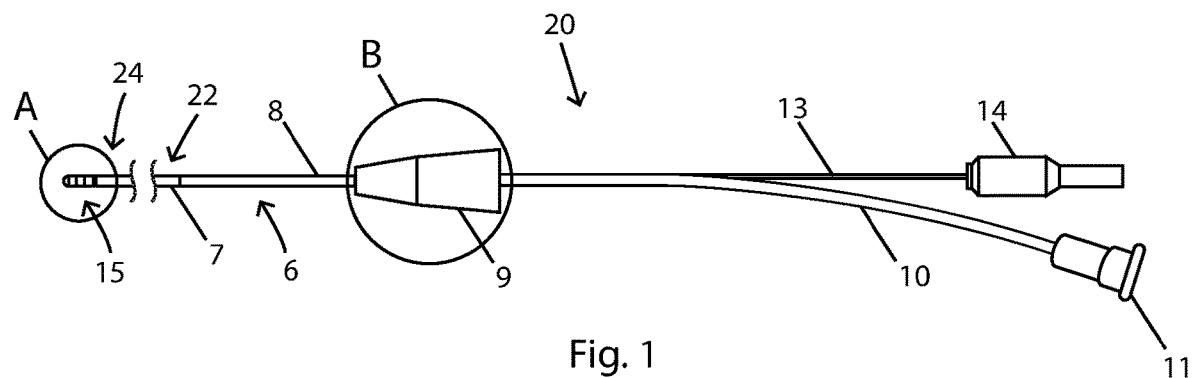
FIG. 1 is an embodiment of a medical device with a generally straight elongate member.

Medical Device (Straight Embodiment) (FIG. 1)

FIG. 1 illustrates an embodiment of a medical device 20 that comprises an elongate member 6 having a proximal region 22 and a distal region 24, and an energy delivery device 15 associated with the distal end of device 20. (Energy delivery device 15 is shown in greater detail in FIG. 2 and FIG. 5.) Elongate member 6 has a tubular configuration defining at least one lumen 26 (shown in FIG. 2) extending substantially throughout its length, and is electrically conductive for delivering energy along the length of elongate member 6 to energy delivery device 15. In some embodiments, elongate member 6 is a hypotube. In typical embodiments, elongate member 6 defines at least one aperture 25 (shown in FIG. 2) at or near the distal end of elongate member 6 or medical device 20. The distal aperture and the lumen defined by the elongate member combine to form a pressure transmitting lumen, whereby fluid pressure from an external environment on the aperture is transmitted through a column of fluid located in the lumen to be measured at a proximal portion of the device. For example, the medical device may be coupled to a pressure sensing mechanism, such as a pressure sensor, to measure the pressure transmitted through the lumen. Medical device 20 further comprises a hub 9 (shown in detail in FIG. 3) associated with the proximal region 22 of elongate member 6. While the embodiment of elongate member 6 of FIG. 1 is biased towards a straight configuration, elongate member 6 is flexible enough to bend when advanced through a curved lumen. Some alternative embodiments of elongate member 6 include a curved portion, for example, the embodiment of FIG. 7.

Figure 2:
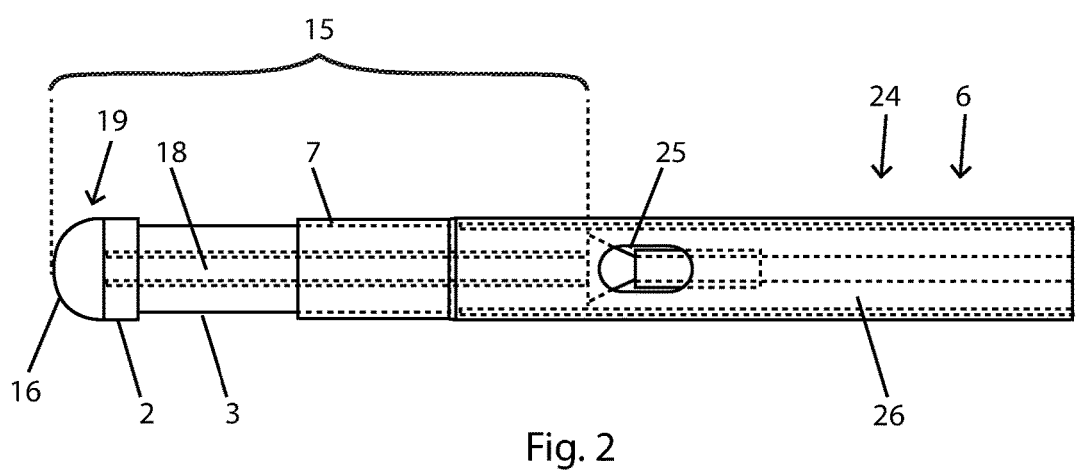
FIG. 2 is an illustration of detail A of FIG. 1.

Distal Portion of Medical Device (FIG. 2)

Elongate member 6 and energy delivery device 15 are electrically coupled by one or more of a variety of connecting means. For example, connecting means may include welding (including laser welding), soldering, electrically conductive adhesives, and/or press fitting.

Elongate member 6 is typically made from different electrically conductive materials. Examples of materials include stainless steel, copper, nickel, titanium, and alloys thereof. Some embodiments of elongate member 6 comprise a stainless steel hypotube or a nitinol hypotube.

The FIG. 2 embodiment of a distal portion of medical device 20 comprises an insulation layer 7 disposed on top of, or around, the distal region 24 of elongate member 6. Insulation layer 7 extends substantially from proximal region 22 to distal region 24 of elongate member 6. Insulation layer 7 may be made from an electrically insulative material such as PEBAX® (polyether block amide), PEEK (Polyether ether ketone), PTFE (Polytetrafluoroethylene), or another thermoplastic material. The FIG. 2 embodiment illustrates insulation layer 7 extending over a proximal portion of thermal shield 3.

Some embodiments of medical device 20 include elongate member 6 defining one or more aperture(s) 25, as shown in FIG. 2. Aperture(s) 25 facilitate fluid communication between the outside environment and lumen 26.

Figure 3:
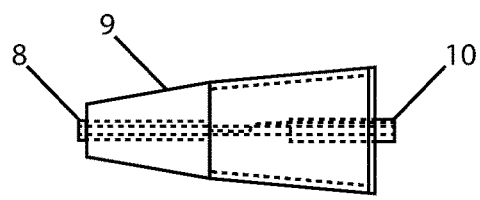
FIG. 3 is an illustration of detail B of FIG. 1.

Hub (FIG. 3)

Some embodiments of medical device 20 include a hub 9 that typically functions as a handle for a user. Alternative embodiments of medical device 20 include an alternate hub 9, such as the examples of FIG. 7 and FIG. 17.

In some embodiments, for example, the embodiments of FIGS. 1 and 3, proximal region 22 is coupled to a hub 9, which is coupled to flexible tubing 10, whereby proximal region 22 is in fluid communication with fluid connector 11. In certain embodiments, flexible tubing 10 is comprised of a flexible polymer, such as polyvinylchloride (PVC), or another flexible polymer, or Tygon®. Connector 11 is structured to be operatively connected to a source of fluid, such as a syringe or an aspirating device, or to a pressure sensing device, such as a pressure transducer.

Medical device 20 also includes means for electrically coupling proximal region 22 of elongate member 6 to an energy source. Proximal region 22 connects to hub 9. Insulated wire 13 is electrically coupled to proximal region 22 within hub 9. The proximal end of insulated wire 13 is connected to electrical connector 14 (e.g. a plug), which is electrically coupled to a source of energy, such as a generator.

Strain relief 8 (shown in FIGS. 1, 3, and 7) provides for a transition of stiffness between proximal region 22 of elongate member 6 and hub 9. In other words, strain relief 8 prevents an abrupt change of flexibility and rigidity at the location where hub 9 is connected to elongate member 6. In certain embodiments, strain relief 8 is a flexible layer that covers and surrounds insulation layer 7, for example, heat shrink. Some alternative embodiments do not include strain relief 8.

Figure 4:
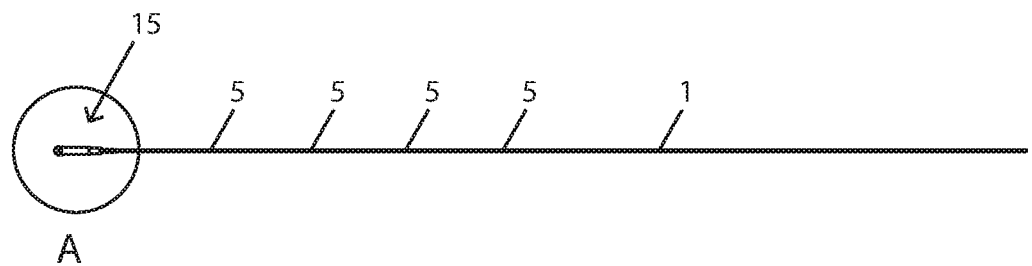
FIG. 4 is an illustration of a spine wire that is biased to be straight and an attached distal region energy delivery device.
Figure 28:
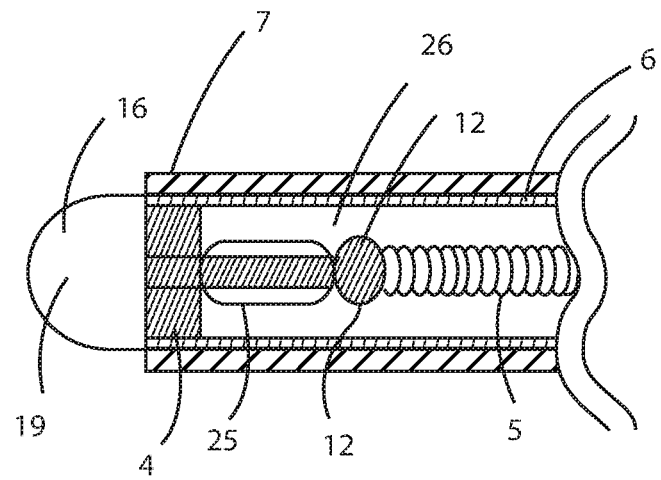
FIGS. 28 and 29 are embodiments with coiled markers.
Figure 29:
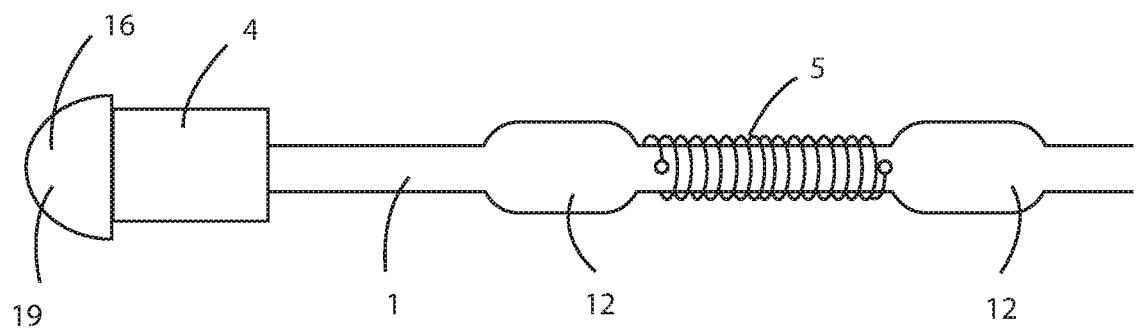

Spine and Markers (FIGS. 4, 28 and 29)

FIG. 4 illustrates an embodiment of support spine 1 (or support wire) that is generally straight and appropriate for use in medical devices 20 that are generally straight, such as medical device 20 of FIG. 1. An energy delivery device 15 and a plurality of evenly spaced radiopaque markers 5 are attached to support spine 1 of FIG. 4.

Figure 6:
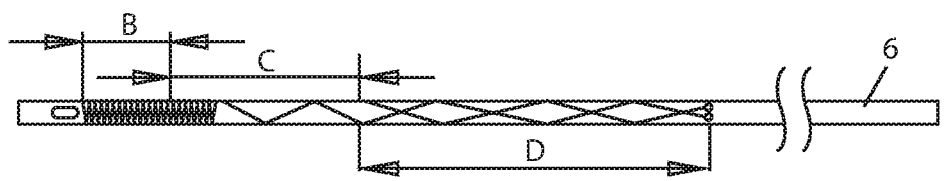
FIG. 6 is an illustration of an elongate member with cuts therein.

In general, there is no minimum spine length and the maximum spine length is limited by the length of the lumen containing the spine. The lumen containing support spine 1 is lumen 26 of elongate member 6, which is typically from about 60 cm to about 120 cm in length. In some embodiments, the support spine 1 (or support wire) extends for a distance of about 10 cm. Various dimensions and specific limitations will be presently described. These specific dimensions and limitations are not mere design choices that would be obvious to one of skill in the art but are rather particularly advantageous for the embodiments of devices and methods described herein. For example, the support spine is typically somewhat longer (for example, a few millimeters longer) than a distal laser-cut section of elongate member 6 (as shown in FIG. 6) to provide overlap with an uncut portion of elongate member 6.

Figure 27A:
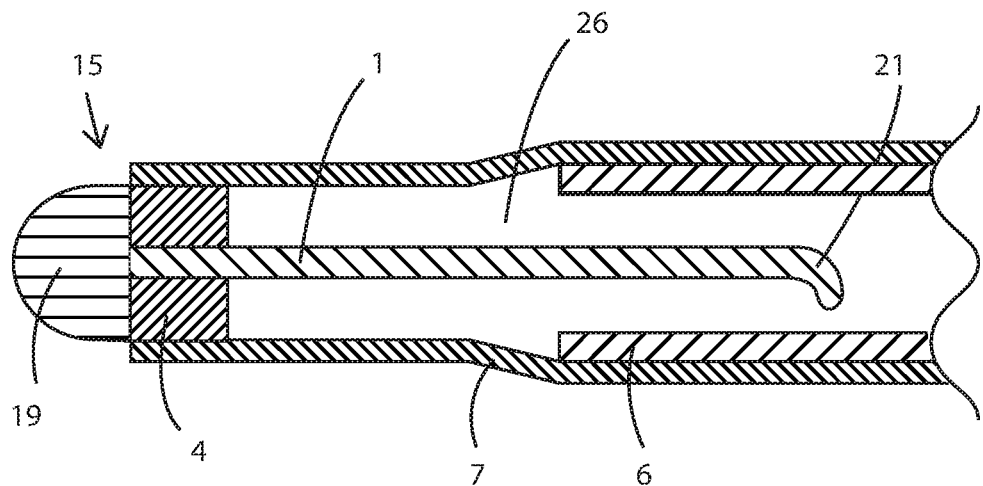
FIGS. 27A and 27B are embodiments with electrically conductive spines.
Figure 27B:
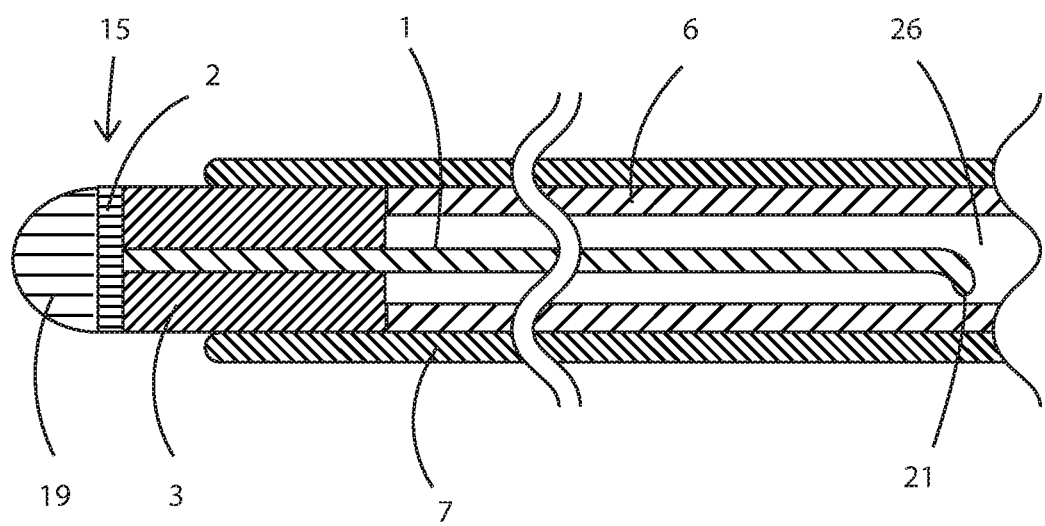

Typical embodiments of support spine 1 have a straight proximal portion. Alternative embodiments of the support spine 1 have a curved proximal end, as shown in FIGS. 27A and 27B. The curved proximal end facilitates contact between the proximal tip of the wire and the side of lumen 26 (i.e. an inner wall of elongate member 6) to establish an electrical connection. Alternative embodiments of support spine 1 that also facilitate contact with elongate member 6 include a support spine comprised of a spring, such as a helical spring or a leaf spring.

Typical embodiments of support spine 1 have a constant outer diameter. Alternative embodiments of support spine 1 can have a varying or non-constant outer diameter. In some embodiments, the support spine tapers proximally and increases in flexibility to facilitate contact with elongate member 6 (i.e. bends more easily to contact the inside surface of elongate member 6) and thereby provide an alternative electrical path to electrode 19.

For ease of manufacturing, typical embodiments of support spine 1 are comprised of one wire. Alternative embodiments of support spine 1 are comprised of two or more wires joined side-by-side to provide a preferential bending direction, or two or more wires braided together for greater strength and flexibility.

For ease of manufacturing, typical embodiments of support spine 1 are comprised of a solid wire. Alternative embodiments of support spine 1 are comprised of a ribbon to provide a preferential bending plane or direction.

For ease of manufacturing, typical embodiments of support spine 1 have a circular cross-section. Alternative embodiments of support spine 1 can have non-circular cross-sections, for example, D-shaped, triangular, or rectangular, which have preferential bending directions.

Radiopaque markers 5 are used to highlight the location of important landmarks on medical device 20. Such landmarks may include the location of energy delivery device 15 or the location of any aperture(s) 25. In general, the radiopaque markers provide the radiopacity to more readily visualize the device under fluoroscopy or other medical imaging modalities. Some embodiments of marker 5 are comprised of platinum. Furthermore, some embodiments of energy delivery device 15 include a conductive spacer 4 (as shown in FIG. 27A) that may be comprised of a radiopaque material such as platinum, so that spacer 4 can also function as a visualization marker.

Some alternative embodiments have spiral or a coiled markers 5 rather than band or ring markers, to provide greater flexibility. In the embodiments of FIGS. 28 and 29, coiled markers 5 are installed on support spine 1 with a flare 12 adjacent each end of the marker. Each flare 12 acts as a restraint to prevent coiled marker 5 from moving or travelling along support spine 1. In the embodiment of FIG. 29, each flare 12 is comprised of a flattened portion of support spine 1 (or flattened wire). In alternative embodiments, one or both ends of a coiled marker could be fixed in place by laser welding or crimping. A coiled marker 5 is typically comprised of platinum or tungsten. In the embodiment of FIG. 28, the coiled marker is proximal of the aperture 25 whereby it can help a physician determine the position of the aperture. For example, if the coiled marker 5 is positioned outside (distal) of a dilator, a physician knows that aperture 25 is also located outside of the dilator and could be used to deliver fluids.

Figure 5:
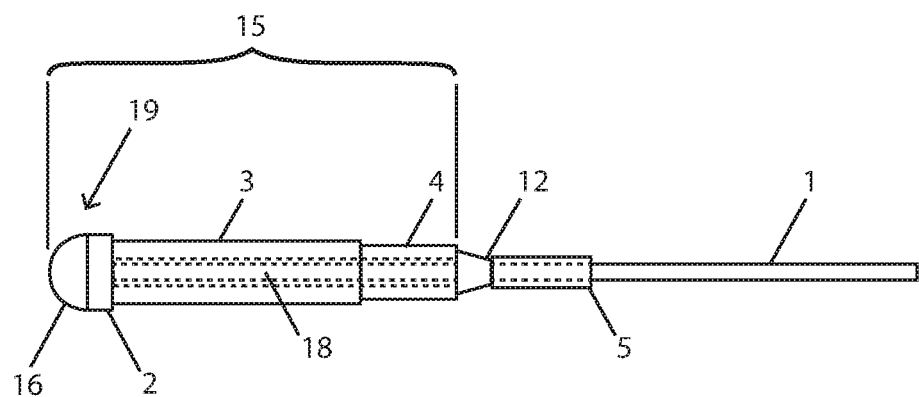
FIG. 5 is an illustration of detail A of FIG. 4.

Energy Delivery Device (FIG. 5)

Some embodiments of energy delivery device 15, such as the embodiment of FIG. 5, are comprised of an electrode 19 attached to and in electrical communication with an intermediate conductive element 18, which is attached to and in electrical communication with conductive spacer 4. Electrode 19 includes support structure 2 and a conductive dome 16. In the embodiment of FIG. 5, support structure 2 is a metallic puck (or disk-shaped element), and in certain embodiments is comprised of tantalum. In some embodiments, conductive spacer 4 is comprised of platinum. The electrode of such embodiments is comprised of electrically conductive material, for example, stainless steels, copper, and/or platinum. In some embodiments, the electrode has a hemispherical, rounded, or domed end. In alternative embodiments, the electrode has other configurations, for example, substantially cylindrical. The electrode is sized for creating a puncture in a tissue of a heart septum while minimizing hemodynamic instability In some embodiments, intermediate conductive element 18 is covered (or surrounded) by a thermal shield 3, which in some examples is a ceramic such as a sapphire ceramic. In alternative embodiments, intermediate conductive element 18 is fabricated from other materials.

The FIG. 5 embodiment of medical device 20 has a support spine 1 that extends proximally of conductive spacer 4 and includes a flare 12. Support spine 1 provides stiffness to the flexible portion of medical device 20 while leaving lumen 26 sufficiently unobstructed for flow of fluids, such as contrast fluid for imaging purposes. In some embodiments, support spine 1 is comprised of nitinol and provides shape memory properties to the device.

In some embodiments, flare 12 is attached to support spine 1, for example, by welding. In alternative embodiments, flare 12 and support spine 1 are integral (i.e. support spine 1 and flare 12 comprise a unitary part). For example, support spine 1 and flare 12 may be produced by the machining of a single piece of cylindrical metal. In some embodiments, flare 12 retains conductive spacer 4 in place. In some embodiments, intermediate conductive element 18 is an extension of support spine 1. In alternative embodiments, intermediate conductive element 18 is a separate part, such as a wire or rod that is distinct from support spine 1.

While electrode 19 is typically attached to the other components of energy delivery device 15 by welding, in alternative embodiments, electrode 19 is operatively coupled to the other components of energy delivery device 15 by alternative means, for example, gluing. In alternative embodiments, such as the embodiment of FIG. 27B, conductive spacer 4 is replaced by other energy delivery elements to facilitate electrical communication between energy delivery device 15 and elongate member 6. The embodiment of FIG. 5 includes a band marker 5, while alternative embodiments include a coiled marker, as described herein above. While the embodiment of FIG. 5 includes metallic parts, alternative embodiments comprise corresponding parts made of non-metallic, electrically conductive materials.

Elongate Member (FIG. 6)

In some embodiments, notches are cut into elongate member 6 to increase flexibility. Cuts may be made by various means, including laser cutting. Different configurations of cuts are possible, including c-cuts, spiral shaped cuts, interrupted spiral cuts, interlocking cuts, and dove-tail cuts. In some embodiments, the cuts traverse the wall thickness of elongate member 6. The distal portion of elongate member 6 may have cuts ranging from about 3 cm in length to substantially the entire length of the shaft of elongate member 6, which is typically from about 60 cm to about 120 cm in length. In certain embodiments, medical device 20 has cuts made into the most distal 10 cm of elongate member 6, and support spine 1 has a length equivalent to or somewhat greater than the length of the cut portion of elongate member 6, i.e., about 10 cm to 11 cm.

The embodiment of FIG. 6 comprises cuts into elongate member 6 that include constant pitch portion B, variable pitch portion C, and dual pitch portion D. Having a smaller pitch (i.e. the cuts being closer together) increases the flexibility of elongate member 6. For example, the distal part of variable pitch portion C has a smaller pitch than the proximal part of portion C and consequently is more flexible. Portion D has a dual pitch (i.e. two cut lines), which further increases the flexibility of elongate member 6 in that portion. In an alternative embodiment, all of sections B, C, and D have dual pitches.

A more flexible distal region 24 facilitates navigation through conduits in a patient's body, such as blood vessels, while a stiffer proximal region 22 facilitates pushability, and resistance to kinking (i e cross-sectional area collapse) under axial compression force. Also, a stiffer proximal region 22 improves torque response at the distal tip to forces applied at the proximal portion of the device.

The flexibility of an embodiment of elongate member 6 depends on its wall thickness and/or outer diameter. To vary flexibility along the length of the elongate member 6, alternative embodiments of elongate member 6 may have varying wall thickness with a constant outer diameter along its length, and/or varying outer diameter with a constant wall thickness along its length.

In some embodiments of medical device 20 in which elongate member 6 is biased to be straight, the shape memory properties and stiffness of support spine 1 allow medical device 20 to behave similarly to a guide-wire and revert to a straight configuration after bending. Such embodiments of support spine 1 also provide stiffness to balance the flexibility created by any cuts made into elongate member 6.

In some embodiments of the medical device 20, the outer diameter of elongate member 6 ranges from about 0.010" (0.025 mm) to about 0.050" (0.13 mm). In some embodiments, the inner diameter of elongate member 6 ranges from about 0.005" (0.013 mm) to about 0.030" (0.076 mm), or, in some embodiments, from about 0.020" (0.051 mm) to about 0.030" (0.076 mm). The length of elongate member 6 is between about 60 cm and about 120 cm. In a specific embodiment, elongate member 6 has in an inner diameter of about 0.025 inches (0.064 cm) and an outer diameter of about 0.029 inches (0.074 cm). In another specific embodiment, elongate member 6 has an inner diameter of about 0.0265 inches (0.067 cm) and an outer diameter of about 0.0325 inches (0.083 cm). The dimensions of elongate member 6 depend on factors such as the distance to the target site, the tortuosity and/or diameter of the vessel(s) to be navigated, whether or not the elongate member is exchange length, as well as any other requirements imposed by auxiliary devices to be used with elongate member 6. For example, elongate member 6 may be sized to be compatible with a particular sheath and/or dilator.

Figure 17:
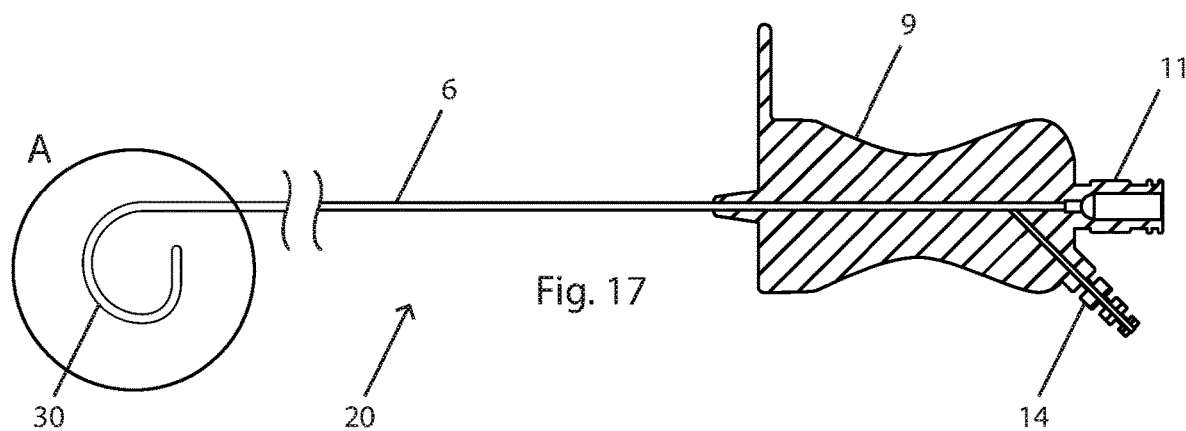
FIG. 17 is a partial cut-away view of the embodiment of FIG. 7.

Medical Device (Embodiment with Curve) (FIGS. 7 and 17)

Some embodiments of medical device 20 include elongate member 6 comprising a distal curved portion 30 with a distal end 28, as shown in FIG. 7. The embodiment of FIG. 7 includes a hub 9 that also functions as a handle.

FIG. 17 is a partially cut-away view of the embodiment of FIG. 7 that illustrates some details of hub 9. Hub 9 includes fluid connector 11 and electrical connector 14, as well as lumens communicating with the connectors.

Distal Curved Portion (FIGS. 7, 8, 9, 10, 12 to 16, 18, 20 to 22, and 24)

Figure 10:
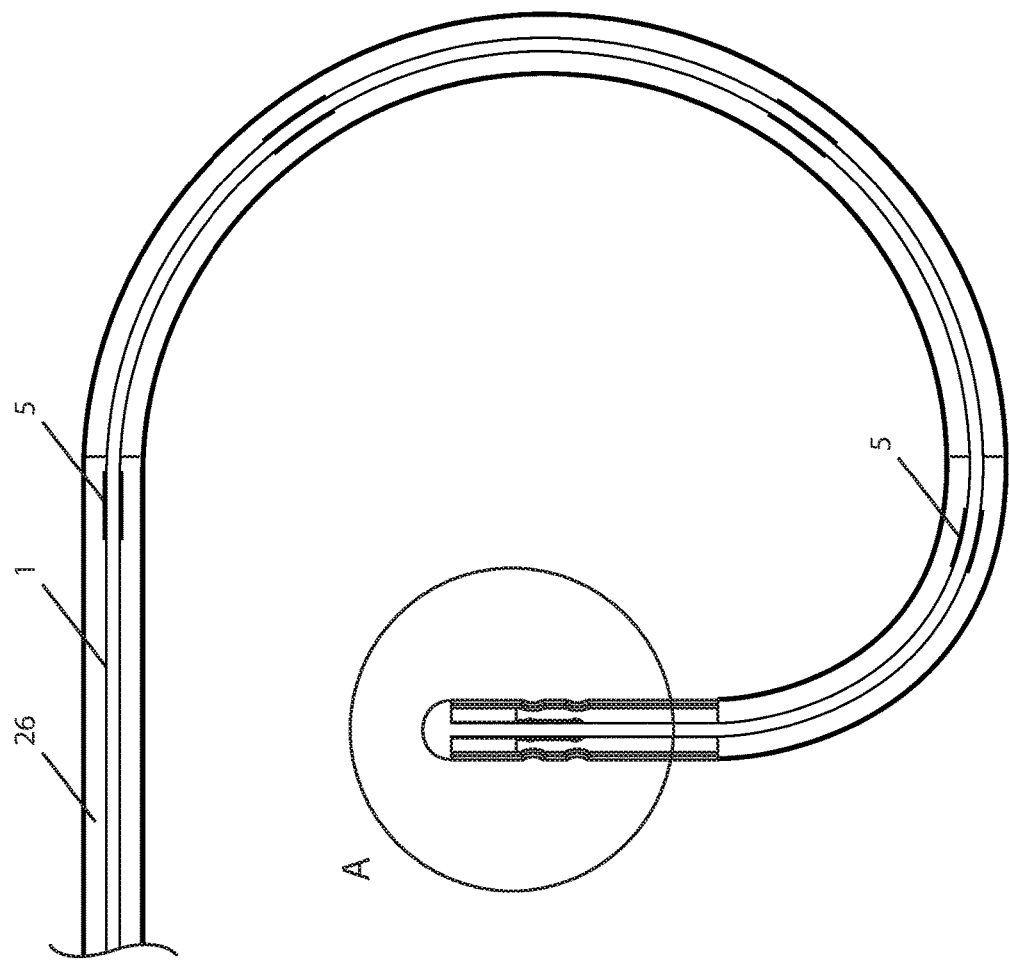
FIG. 10 is a cut-away view of the embodiment of FIG. 8.
Figure 13:
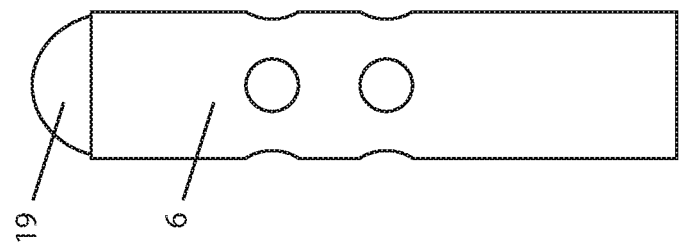
FIG. 13 is an illustration of detail A of FIG. 12.
Figure 12:
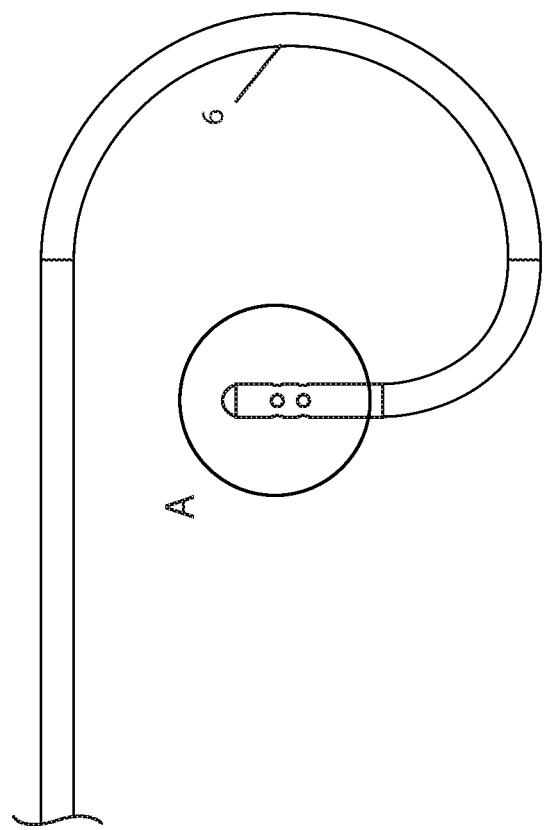
FIG. 12 is an illustration of the embodiment of FIG. 8 with no external insulation layer.

Distal curved portion 30 of the embodiment of FIG. 7 is shown in detail in FIG. 8, with a cut-away view shown in FIG. 10. FIGS. 12 and 13 are illustrations of the embodiment of FIGS. 8 and 9 with insulation layer 7 removed. The embodiment includes apertures 25 for allowing fluid flow between lumen 26 and the environment outside of medical device 20, and an electrode 19 for delivering electrical energy, such as radiofrequency electrical energy (RF), to a treatment site. FIG. 9 illustrates detail A of FIG. 8 and includes enlarged views of apertures 25 and the electrode 19. Curved portion 30 is sufficiently flexible so that it may be substantially straightened when it is inserted into a straight tube or vessel, and may bend or curve when advanced through curved vasculature or other body lumens, or when exiting the straight tube or vessel. Consequently, embodiments of medical device 20 having distal curved portion 30 may be used with a sheath and/or dilator for advancement through body lumens.

Embodiments of medical device 20 having a distal curved portion 30 similar to that of FIG. 8 typically have a support spine 1 that adopts a curved distal portion similar to the example of FIG. 14 once installed within the elongate member 6. The embodiment of FIG. 14 also illustrates band markers 5 and energy delivery device 15. FIG. 15 is a cut-away view of the embodiment of support spine 1 of FIG. 14. FIG. 16 is an illustration of the area marked "A" in FIG. 15. Energy delivery device 15 of the embodiments illustrated in FIGS. 15 and 16 is comprised of a conductive dome 16 and conductive spacer 4.

Figure 20:
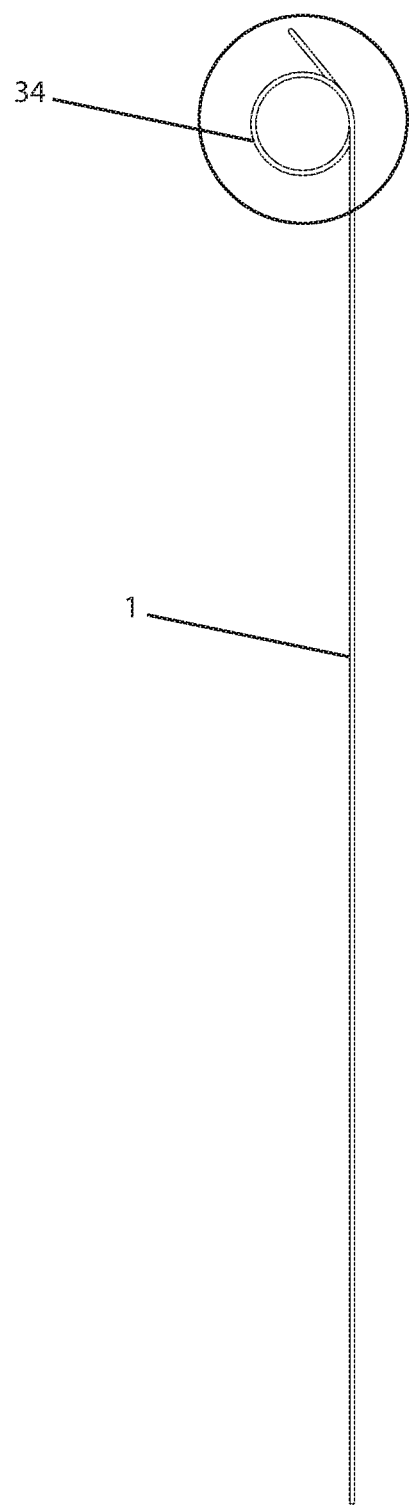
FIG. 20 is an illustration of an embodiment of a support spine for a version of the medical device with a distal curve, before the spine is installed.
Figure 21:
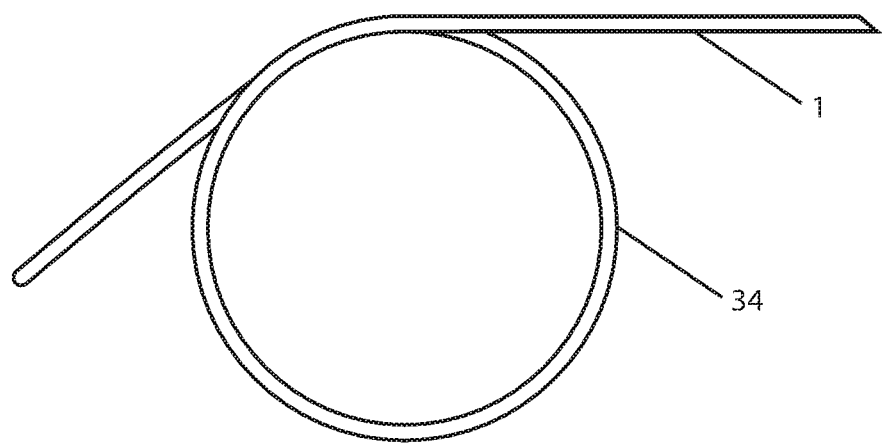
FIG. 21 is an illustration of detail A of FIG. 20.
Figure 22:
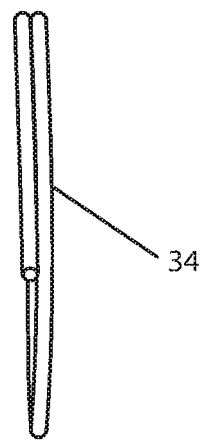
FIG. 22 is an end view of the embodiment of FIG. 21.

FIGS. 20 to 22 illustrate an embodiment of a support spine 1 before installation within elongate member 6 of an embodiment of the medical device 20 with a curved distal portion. FIG. 20 shows an entire support spine 1 including coiled portion 34. FIG. 21 is an illustration of detail A of FIG. 20, showing an enlargement of coiled portion 34. FIG. 22 is an end view of the embodiment of FIG. 21. In this embodiment, support spine 1 overlaps itself in the coiled portion 34. Support spine 1 is elastically biased towards a curved or looped configuration prior to being inserted into lumen 26 of elongate member 6.

A curved support spine 1 acts to bias a portion of medical device 20 to have a curved section, while elongate member 6 is typically biased towards a straight configuration. Therefore, when support spine 1 of FIG. 20 is installed within a straight elongate member 6, the biasing force of support spine 1 and the biasing force of elongate member 6 act against each other, resulting in a curved portion 30 of medical device with a curvature between that of coiled portion 34 of support spine 1 and straight elongate member 6. An example of a curved portion 30 of medical device 20 is shown in FIG. 8. FIG. 8 illustrates one possible configuration of a curved portion. Alternative embodiments of medical device 20 may have a curved portion with a different shape or configuration, for example, the curved portion may have a different size and/or radius of curvature.

In an assembled medical device 20 with a curved portion 30 (such as the embodiment of FIG. 8), support spine 1 is typically positioned against the inner radius side of lumen 26 through most of curved portion 30. However, for illustrative purposes in the drawings, support spine 1 is shown substantially centered within lumen 26.

Figure 18:
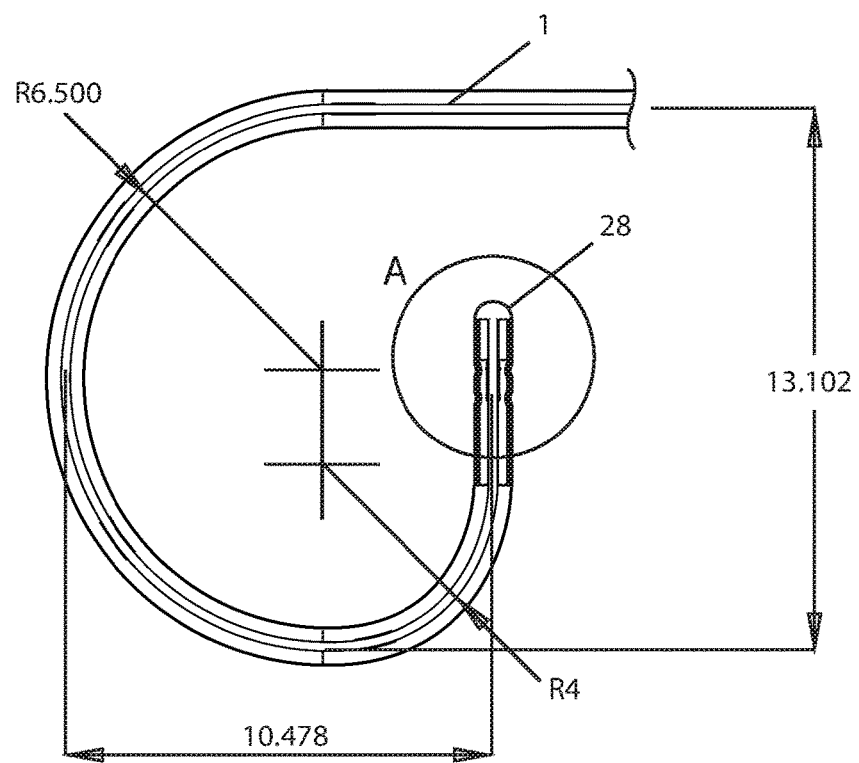
FIG. 18 is a cut-away view of detail A of FIG. 17.

An embodiment of curved portion 30 of medical device 20 is shown in FIG. 18, which is a cut-away view of detail A of FIG. 17. The particular embodiment of FIG. 18 includes a substantially 270 degree curve having a length of about 10.5 mm (±50%), and a lateral dimension of about 13.1 mm (±50%). The first 90 degrees of the curve has a radius of about 6.5 mm (±50%), and the last 90 degrees of the curve has a radius of about 4 mm (±50%). The curve is sized to fit inside structures of human anatomy, for example, a left atrium.

In embodiments of medical device 20 that are substantially biased towards a straight configuration when assembled, such as the examples of FIGS. 1 to 6, it is typical for support spine 1 to be biased towards assembled straight configuration as well.

Alternative Embodiments

Both of the two above mentioned embodiments of medical device 20 (generally straight and straight with a curved distal end portion) use a support spine 1 (or support wire) that is pre-shaped to provide the device with a "default" position. The device is normally biased towards the default position, which is not permanently altered by interaction with anatomy when the user advances the device through body lumens or other structures. In other words, medical device 20 is resilient and returns to its original form after being bent or otherwise manipulated from its default shape.

Some straight embodiments of medical device 20 that include an energy delivery device 15 facilitate forward linear advancement along a substantially straight line, and may be used for cutting and channeling through tissue, such as CTOs (chronic total occlusions). Embodiments of medical device 20 that have a distal curved portion 30 and an energy delivery device 15 may be used for cutting through other types of tissue that are more readily accessible using curved devices, such as a septum of the heart in a transseptal procedure. Typically, in performing a transseptal procedure, the user advances medical device 20 through a support catheter to position the electrode against a septum. After perforation of the septum, the user further advances the device through the tissue, whereupon embodiments with a distal curved portion orient the electrode towards the center of the curl and away from the opposite heart chamber wall. This configuration increases patient safety by reducing the risk of accidental perforation of a heart wall or other vital structure.

While specific embodiments and uses are disclosed herein, all of the above described embodiments of medical device 20 can be used in applications involving channeling through tissue, such as CTOs, or for general tissue puncture, such as transseptal procedures. Furthermore, some embodiments include a heat shield (as shown in FIG. 2) and other embodiments do not include a heat shield (as shown in FIG. 11).

Figure 11:
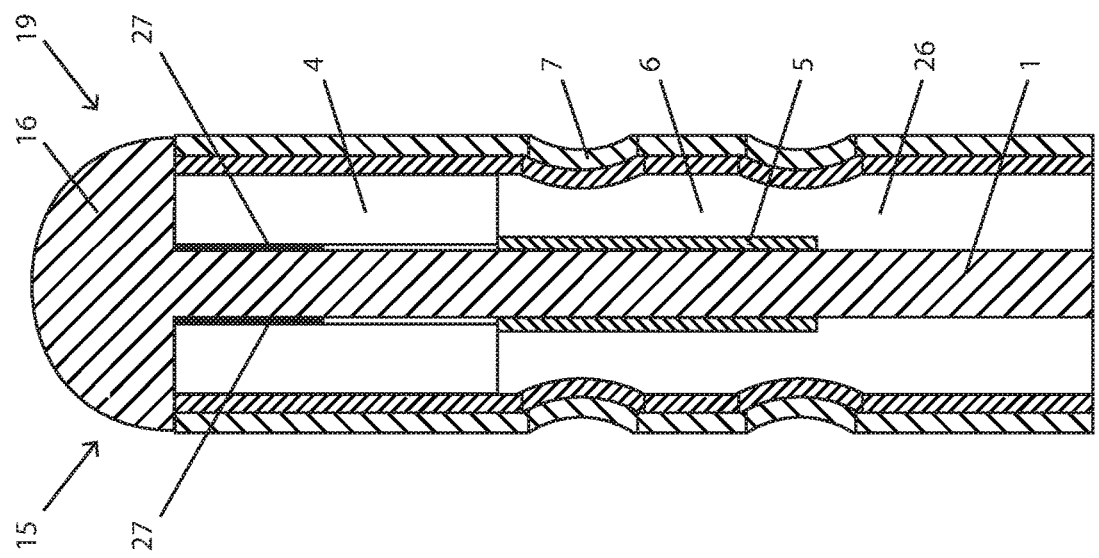
FIG. 11 is an illustration of detail A of FIG. 10.
Figure 19:
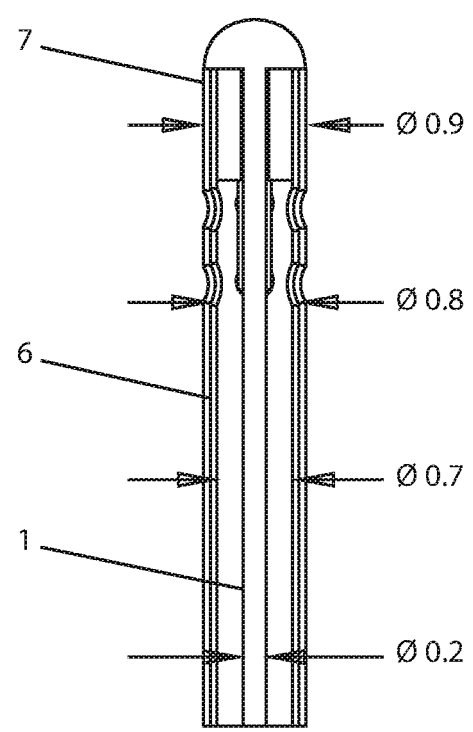
FIG. 19 is an illustration of detail A of FIG. 18.

Energy Delivery Device of a Curved Embodiment (FIGS. 11, 19, 26)

FIG. 11 shows a close-up view of detail A of FIG. 10. The embodiment of FIG. 11 includes energy delivery device 15 comprised of conductive dome 16 and spacer 4. In some embodiments, dome 16 is formed by end-welding a portion of support spine 1 that extends distally through the bore of spacer 4. The heat from welding support spine 1 also welds conductive dome 16 with the distal end surface of spacer 4, as well as welding a distal portion of support spine 1 to a distal portion of spacer 4 to form weld 27. In alternative embodiments, weld 27 has a different configuration than in the example of FIG. 11, for example, it may extend proximally a greater or lesser distance.

The example of FIG. 11 includes a conductive spacer 4 electrically coupled with elongate member 6, typically by tack welding. In alternative embodiments, conductive spacer 4 and member 6 are joined by other methods, including electrically conductive adhesives, solder, laser welding, and/or press fitting. In some alternative embodiments, dome 16 is formed by machining cylindrical stock integral with support spine 1. In other alternative embodiments, an electrode may be attached to the end of medical device 20 by engaging other portions of the device using, for example, a friction fit. In some alternative embodiments, portions of the support spine 1, spacer 4, and elongate member 6 are welded substantially concurrently to form the dome and join the parts together.

In the embodiment of FIG. 11, conductive dome 16 is in direct contact with the distal end surface of elongate member 6, and support spine 1 extends proximally from conductive dome 16 within lumen 26 of elongate member 6. Elongate member 6 is covered by insulation layer 7, leaving conductive dome 16 electrically exposed to define an electrode 19. FIG. 11 also illustrates a band marker 5 attached to support spine 1. Band marker 5 marks or highlights the position of some apertures without increasing the outer diameter of medical device 20, as it is located within a lumen 26 of elongate member 6.

FIG. 11 illustrates that elongate member 6 is in electrical communication with spacer 4 and electrode 19. When in use, electrical energy flows from elongate member 6 to electrode 19 either directly from elongate member 6 or via spacer 4.

FIG. 19 illustrates a close-up of detail A of FIG. 18 and shows a specific embodiment of the distal end portion of medical device 20. Insulation layer 7 has an outer diameter of about 0.9 mm (0.0365 inches), elongate member 6 has an outer diameter of about 0.8 mm (0.0325 inches) and an inner diameter of about 0.7 mm (0.0265 inches), and support spine 1 has an outer diameter of about 0.2 mm (0.008 inches). Alternative embodiments have other dimensions for these features as disclosed in application Ser. No. 61/781,231, entitled "Electrosurgical Device Having a Lumen". In some alternative embodiments, insulation layer 7 has an outer diameter between about 0.5 mm to about 1.0 mm, or, more specifically, about 0.7 to about 1.0 mm; elongate member 6 has an outer diameter between about 0.4 mm to about 0.9 mm, or, more specifically, between about 0.6 and about 0.9 mm; elongate member 6 has an inner diameter between about 0.3 mm to about 0.8 mm, or, more specifically, between about 0.5 mm to about 0.8 mm; and support spine 1 has an outer diameter between about 0.1 mm to about 0.3 mm. The small diameter of support spine 1 minimizes the obstruction of lumen 26 and thereby facilitates fluid flow. It also imparts flexibility to the spine so that it may make contact with the electrically conductive inner surface of the elongate member. The electrode of FIG. 19 has a diameter substantially the same as the insulation layer's outer diameter of between about 0.5 mm to about 1.0 mm (about 0.9 mm in the illustrated embodiment). In one particular embodiment, insulation layer 7 has an outer diameter of about 0.96 mm (0.038 inches) and support spine 1 has an outer diameter of about 0.25 mm (0.010 inches), with the inner and outer diameters of elongate member 6 falling between these two values.

Instead of, or in addition to, electrical energy being delivered to electrode 19 via elongate member 6, electrical energy may be delivered to electrode 19 through support spine 1. An elongate configuration of support spine 1 is illustrated in FIGS. 14 and 15. Due to its elongate shape, support spine 1 is typically floppy (i.e. hanging loosely at its proximal end) and not self-supporting. As a result, once support spine 1 is installed within lumen 26 of elongate member 6, a proximal end or portion of support spine 1 is normally in contact with a wall of lumen 26 such that electrical energy from elongate member 6 can flow through support spine 1 to electrode 19. As such, support spine 1 can provide a secondary pathway for electrical energy to electrode 19.

Another aspect of support spine 1 is illustrated in the example of FIG. 26. Support spine 1 is drawn using hatch-marks to indicate that it is a different material than elongate member 6. The hatch-marks are not intended to depict cuts in support spine 1, however, support spine 1 may, or may not, have cuts made therein or therethrough. FIG. 26 illustrates an embodiment of elongate member 6 with cuts in a distal portion starting at the point labeled "C". The individual cuts are not shown in the figure. In this embodiment, the support wire (or spine) extends proximally beyond point "C". During use, at least a proximal portion of support spine 1 is typically in contact with a wall of lumen 26 (not shown in FIG. 26). As such, electrical energy from elongate member 6 can flow through support spine 1 to energy delivery device 15, as described herein above. In this specific example, support spine 1 extends proximally beyond the cut portion of elongate member 6, (i.e. the proximal end of the support spine overlaps with an uncut portion of the elongate member). This configuration allows support spine 1 to act as a backup or secondary electrical pathway in the case of a breakage or interruption in the pathway through the cut portion of elongate member 6.

Distal End Attachment of Support Spine (FIGS. 11 and 26)

In typical embodiments of medical device 20, support spine 1 is connected at the distal end of the medical device 20 and extends proximally therefrom, while the proximal end of support spine 1 remains un-attached to, and independent of, elongate member 6 (or any other part of medical device 20).

Typically, support spine 1 extends proximally from the energy delivery device. While the embodiments of FIGS. 1 to 27 illustrate support spine 1 joined to the center of electrode 19 of energy delivery device 15, in alternative embodiments, support spine 1 is attached or otherwise coupled to the device at other locations. For example, an alternative embodiment comprises a closed-ended lumen with the support wire (or spine) attached off-center. Another alternative embodiment comprises an open-ended lumen with the support wire attached to a side-wall defining the lumen about the distal end of medical device 20.

As noted herein above, the proximal end of support spine 1 is independent of the side of lumen 26 (i.e. it is not fixed to the side of the lumen). This configuration allows the proximal end of support spine 1 to move longitudinally and laterally relative to the inner wall of the elongate member, which allows the distal end of medical device 20 (where the support spine 1 and elongate member 6 are joined) to bend or curve unimpeded by support spine 1. The ability of the distal end portion of medical device 20 to bend or curve facilitates advancement of the device through tortuous vasculature and other body vessels.

Furthermore, the proximal end of support spine 1 is unattached to medical device 20 so that it does not constrain the curvature of the device. Elongate member 6 and support spine 1 have different bend radii as a result of differences in the bend axis due to the wall thickness of the elongate member 6 and the position of the support spine 1. When the medical device 20 is bent about its distal portion, the difference in bend radius results in different arc lengths for elongate member 6 and support spine 1. If the support spine 1 was fixed at a proximal portion of medical device 20, the arc-lengths of elongate member 6 and support spine 1 would be fixed, and the catheter curvature would be constrained. In some embodiments, fixing the arc-lengths of elongate member 6 and support spine 1 is beneficial if constraining the curvature of the medical device 20 is desirable (i.e. if a user desires to limit the amount of bending applied to a distal portion of medical device 20).

Elongate Member with a Discontinuous Spiral Cut and Support Spine (FIGS. 25A and 25B)

FIG. 25A is a diagram of a portion of an embodiment of medical device 20 showing a substantially straight portion of elongate member 6 with an interrupted (or discontinuous) spiral cut 32 through its sidewall. Some embodiments of elongate member 6 have an interrupted spiral cut 32 comprising a cut of about 120 degrees around the circumference of elongate member 6, followed by about 30 degrees of un-cut material around the circumference. Alternative embodiments include a different cut pattern. The embodiment of FIG. 25A includes a generally straight support spine 1 within lumen 26 (represented in broken line).

FIG. 25B illustrates the embodiment of FIG. 25A with a bend or curve. In this configuration, side "L" of elongate member 6 is in tension, while side "R" is in compression. The uncut portions of the sidewall of elongate member 6 are indicated by the letter "U". Uncut portions on side L are being stretched, pulled, or spread apart resulting in spiral cuts 32 on the tensile side larger than the cuts in FIG. 25A, where the device is shown in its straight configuration. The uncut portions (U) on side R are being compressed, pushed, or squeezed together resulting in spiral cuts 32 on the compressive side smaller than the cuts shown in FIG. 25A.

While FIG. 25A shows the elongate member in a straight configuration with support spine 1 positioned centrally within lumen 26, FIG. 25B shows the elongate member in a curved configuration with support spine 1 positioned against the tensile side of elongate member 6. In this position, support spine 1 provides support for the tensile side of elongate member 6 by distributing the stress of the bend or curve along a longer length of elongate member 6 than in the case of an unsupported elongate member (i.e. an elongate member without a spine). Consequently, the stress of the bend is spread amongst more cuts 32 and uncut portions of the sidewall (U), resulting in reduced risk of damage to elongate member by the stress forces of the bend or curve. Thus, the support spine 1, as shown in FIG. 25B, assists in distributing the load along elongate member 6. Furthermore, since an applied load also deflects the support spine, the support spine takes some of the load directly.

In some embodiments, the support spine 1 allows elongate member 6 to have a smoother curve than is provided by an unsupported elongate member as the support spine functions as a spline. Inclusion of support spine 1 reduces the frequency of abrupt bends along elongate member 6.

In general, a device with a stiffer vessel contacting surfaces (i.e. the surfaces of the device that contact body vessels) cause more trauma to a patient when a user advances it through body vessels than a device with more flexible vessel contact surfaces. The utilization of a support spine to provide some of the required device stiffness allows for a suitably rigid medical device with a relatively more flexible elongate member, which results in a more flexible "vessel contacting surface" and reduces traumatic effects of advancement of the medical device within body vessels. Embodiments of the devices shown in the Figures are covered with a layer of insulation so that the sharp-angled cut surfaces, such as those shown in FIG. 25A, are prevented from making direct contact with the vessel wall.

An embodiment of elongate member 6 with a thinner sidewall and/or a greater number of cuts into the sidewall will have less rigidity (or greater flexibility) than another embodiment with a thicker sidewall and/or a lesser number of cuts (or no cuts), all other factors being equal.

Fluid Flow in Lumen Proximal and Distal Portions (FIG. 26)

Making reference to FIG. 26, typical embodiments of medical device 20 (including both the generally straight embodiment and the embodiment with a distal curved portion 30) include a flexible elongate member 6 that defines a lumen 26, an independent support spine 1 being affixed to the distal end of medical device 20 and extending proximally within the lumen, and apertures 25 that may provide for delivering fluid at the distal end of medical device 20. (Alternative embodiments do not have an aperture 25). For typical embodiments, the support spine 1 extends from the distal end within lumen distal portion 36 such that a lumen proximal portion 35 is substantially unobstructed by the support spine, thereby minimizing effects on fluid flow.

Consider the specific example of an embodiment with a 120 cm elongate member (with a 120 cm lumen), with cuts made in the most distal 10 cm of the elongate member. A distally attached support spine would be between 10 cm and 11 cm in order to support the 10 cm distal cut portion of elongate member. Such a support spine would partially obstruct fluid flow in the distal 10 cm of the 120 cm lumen. A possible alternative device could have support spine 1 attached at the proximal end of lumen 26, however for it to provide support at the distal cut portion of elongate member, it would have to extend the entire length of the lumen (e.g. 120 cm in the case of a 120 cm elongate member), and consequently obstruct fluid flow through the entire length of lumen 26. The distally attached support spine 1 obstructs a much smaller portion of the lumen and has significantly less effect on fluid flow. Minimizing the obstruction of fluid flow facilitates the delivery of fluids, such as fluids used for staining tissue or other imaging purposes.

Electrically Conductive Spine (FIGS. 27A and 27B)

In some embodiments of medical device 20, the support spine 1 functions as the primary (or only) pathway for electrical energy to travel from elongate member 6 to energy delivery device 15. In the example of FIG. 27A, conductive spacer 4 is spaced apart from and not in contact with elongate member 6. Insulation layer 7 is a continuous layer of one material in the embodiment of FIG. 27A, but in alternative embodiments insulation layer 7 could be comprised of more than one type of material. For example, the portion of insulation layer 7 covering elongate member could be one (or more) type(s) of material and the portion of insulation layer 7 distal of elongate member 6 could a different material (or materials). In general, at least some portion of insulation layer 7 distal of elongate member 6 is comprised of electrically non-conductive material, whereby electrical energy cannot flow through insulation layer 7 to energy delivery device 15. The embodiment of FIG. 27A includes a spinal curve 21 at the proximal end of support spine 1 to facilitate contact between support spine 1 and elongate member 6. Other embodiments of medical device 20 could have a bent support spine 1, a generally straight support spine 1 (i.e. lacking spinal curve 21), or a support spine 1 with another configuration. Whether the proximal portion of support spine 1 is curved, bent, straight, or another configuration, support spine 1 is typically sufficiently elongate and floppy to contact elongate member 6 at some position along its length. While spacer 4 is typically a metallic material to facilitate welding electrode 19 to medical device 20 and securing support spine 1, in alternative embodiments, spacer 4 could be a non-metallic material and/or an electrically non-conductive material.

Making reference to FIG. 27B, some embodiments of medical device 20 have a thermal shield 3 comprised of non-conductive material whereby support spine 1 functions as the primary pathway for electrical energy to travel from elongate member 6 to energy delivery device 15. While thermal shield 3 is a single integral part in some embodiments (such as the embodiment of FIG. 27B), in alternative embodiments, thermal shield 3 could be comprised of more than one part and/or material. The embodiment of FIG. 27B does not include a conductive spacer 4 proximal of thermal shield 3, unlike the embodiment of FIG. 5 that has a conductive spacer 4 to enable electrical communication between elongate member 6 and electrode 19. Some embodiments include an energy delivery device 15 comprised of support structure 2 and electrode 19, such as the example of FIG. 27B, while alternative embodiments may have an energy delivery device 15 comprised of a single integral part, or an energy delivery device 15 with another configuration. While the embodiment of FIG. 27B includes a spinal curve 21, alternative embodiments of medical device 20 have a proximal portion of support spine 1 that is bent, straight, or another configuration. Alternative embodiments include a flare 12, as previously described in reference to FIG. 5. In both of the embodiments illustrated in FIGS. 27A and 27B, a non-conductive material restricts or impedes the electrical pathway from elongate member 6 to electrode 19 such that support spine 1 is the primary (or only) pathway of electrical conductivity between elongate member 6 and electrode 19. The non-conductive material could be, for example, a ceramic or a polymer.

Generator

Medical device 20 may be used in conjunction with any source of energy suitable for delivery to a patient's body. Sources of energy may include generators of ultrasonic, microwave, radiofrequency, or other forms of electromagnetic energy. In embodiments utilizing ultrasonic energy, energy delivery device 15 typically comprises an ultrasound transducer. In one particular embodiment, the source of energy is a radiofrequency (RF) electrical generator, such as a generator operable in the range of about 100 kHz to about 3000 kHz, designed to generate a high voltage in a short period of time. More specifically, the voltage generated by the generator may increase from about 0 Vrms to greater than about 400 Vrms in less than about 0.6 seconds. The maximum voltage generated by the generator may be between about 180V peak-to-peak and about 3000V peak-to-peak. The waveform generated may vary, and may include a sine-wave, or a rectangular-wave, amongst others. In some embodiments, because of the small size of the electrode, the impedance encountered during RF energy application may be very high. The generator may be operable to continue to maintain the voltage even with low or fluctuating tissue impedance. For example, energy may be delivered to a tissue within a body at a voltage that rapidly increases from 0 V to 400 V. Different embodiments of generators have power capabilities of 0 to 25 watts, 0 to 50 watts, or 0 to 300 watts.

Methods

An operator may use medical device 20 to deliver energy to a target site within a body of a human or animal. In some embodiments, the energy is RF current, and the energy punctures or creates a void or channel in the tissue at the target site. Further details regarding delivery of energy to a body are found in U.S. patent application Ser. No. 10/347,366 (filed on Jan. 21, 2003), Ser. No. 10/760,749 (filed on Jan. 21, 2004), Ser. No. 10/666,288 (filed on Sep. 19, 2003), and Ser. No. 11/265,304 (filed on Nov. 3, 2005), and U.S. Pat. No. 7,048,733 (application Ser. No. 10/666,301, filed on Sep. 19, 2003), all of which are incorporated herein by reference.

In one specific embodiment of a method of use of the present invention, an operator uses the medical device to deliver RF energy to a target tissue to create an insulative vapor layer around the electrode, thereby resulting in an increase in impedance. For example, the impedance may increase to greater than 1500Ω. Increasing the voltage increases the intensity of fulguration, which may be desirable as it allows for an increased tissue puncture rate. An example of an appropriate generator for this application is a BMC RF Puncture Generator (model numbers RFP-100 and RFP-100A, Baylis Medical Company, Montreal, Canada). These generators are operable to deliver continuous RF energy at about 480 kHz. A grounding pad or dispersive electrode is connected to the generator for contacting or attaching to a patients body to provide a return path for the RF energy when the generator is operated in a monopolar mode.

An aspect of the invention is a method of creating a puncture in tissue, for example, using embodiments of a medical device as described herein above. Making reference to FIGS. 23A and 23B, an embodiment of the method comprises (i) introducing a medical device 20 into a body of a patient, the medical device 20 comprising an elongate member 6 having a distal region 24 and a proximal region 22; an energy delivery device 15 proximate to the distal region and capable of cutting material; and a lumen 26 and apertures 25 operable to communicate with a pressure sensing mechanism (not shown) for determining pressure in the body proximate to the distal region 24; (ii) positioning the energy delivery device 15 at a first desired location in the patients body adjacent material to be cut; (iii) delivering energy using the energy delivery device 15 to cut the material; and (iv) measuring pressure in the body using the pressure sensing mechanism in order to determine the position of the medical device 20 before and/or after step (iii). In some embodiments of this aspect, step (ii) comprises delivering fluid, such as contrast fluid, for imaging at the first desired location in the patients body.

Some embodiments of the method further comprise a step (v) advancing the device to a second desired location. In certain embodiments of this aspect, the medical device comprises at least one radiopaque marker 5 and step (v) comprises monitoring at least one of said radiopaque markers 5. Some embodiments of the method comprise a step (vi) measuring pressure at the second location. In some embodiments, the medical device comprises at least one radiopaque marker 5 and step (vi) is performed after confirming the position of the pressure sensing mechanism at the second location using the radiopaque markers.

In some embodiments, step (i) comprises introducing the device into the patients vasculature and/or other body lumens by inserting the device 20 into a dilator 52 and a guiding sheath 50 positioned in the patients vasculature. In certain embodiments, the device 20 and at least one of the dilator 52 and sheath 50 comprise a radiopaque marking, and step (ii) comprises aligning the radiopaque markings to aid in positioning the device. For certain alternative embodiments of the method, step (v) comprises advancing the dilator 52 and the sheath 50 into the second location together over the spatially fixed medical device 20. In other alternative embodiments, step (v) comprises advancing the dilator, sheath, and medical device all together into the second location.

In certain embodiments, the material to be cut is tissue located on an atrial septum 56 of a heart, for example, the fossa ovalis 60 of a heart. In such a case, the pressure measured at the first location is the blood pressure in the right atrium 54, and the pressure measured at the second location is the blood pressure in the left atrium 58.

In some alternative embodiments, the method further includes delivering imaging fluid (i.e. contrast) that is visible using an imaging system in order to confirm the position of the medical device 20 at the second desired location.

Figure 23A:
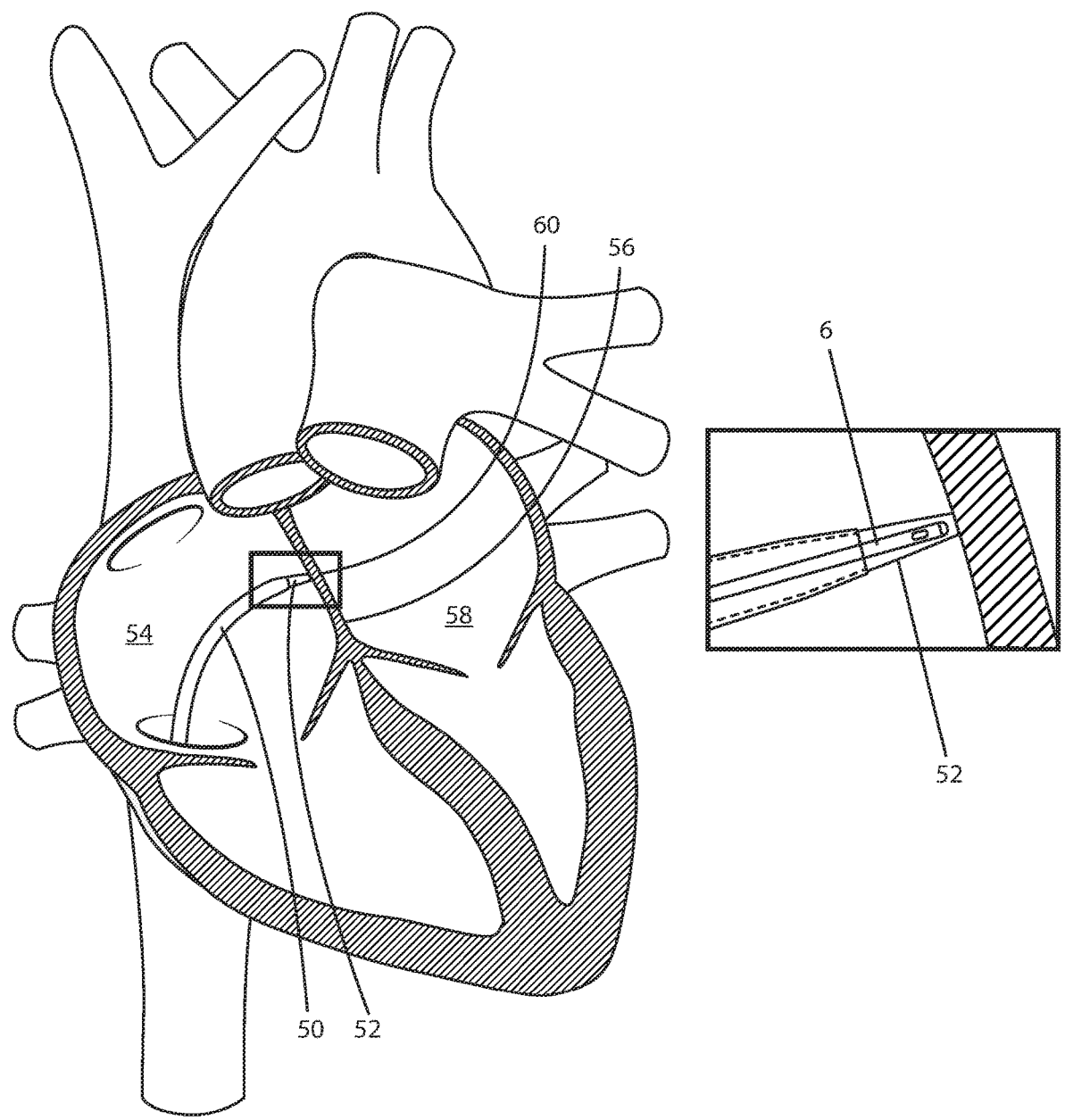
FIGS. 23A and 23B illustrate the before and after stages of a transseptal method.
Figure 23B:
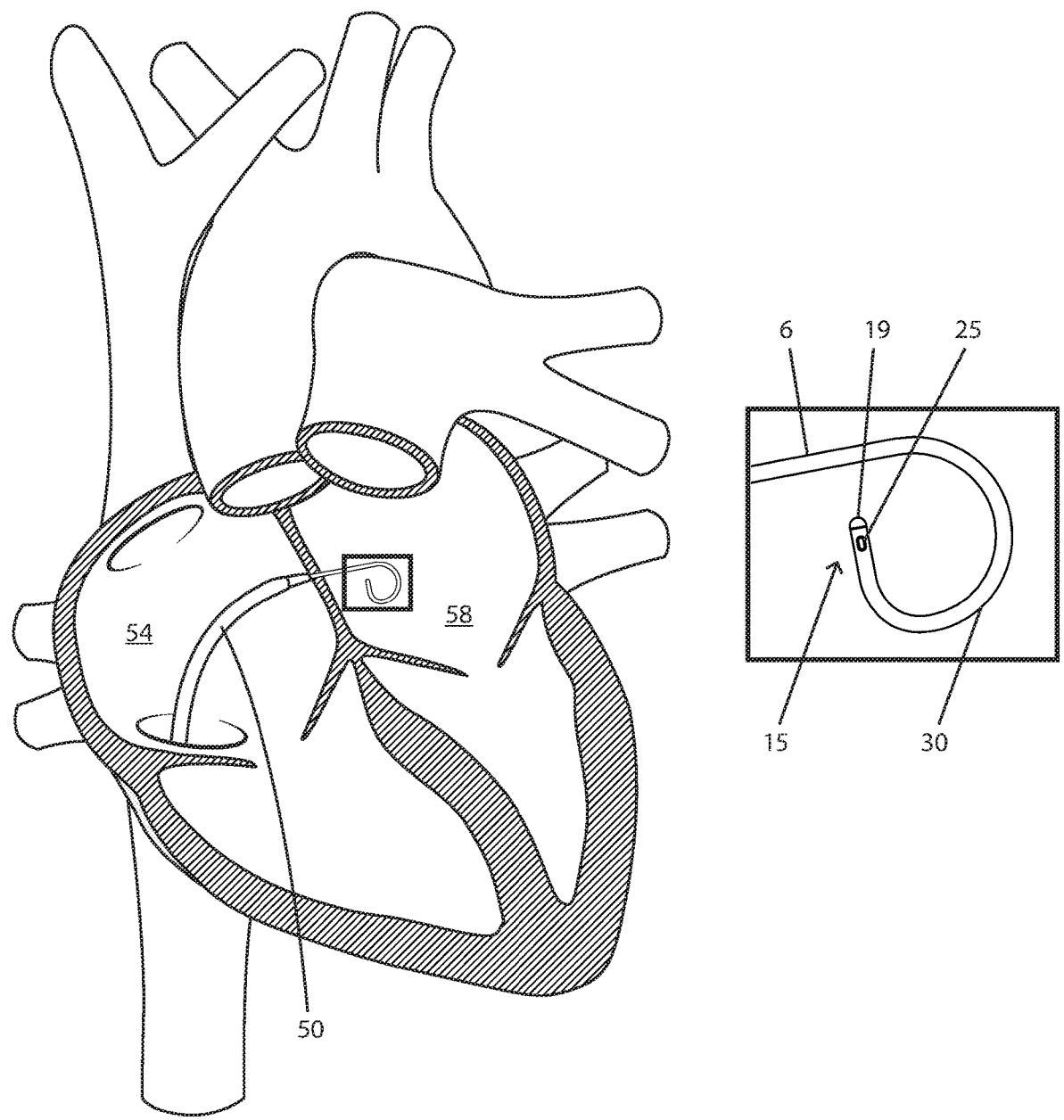
Figure 24:
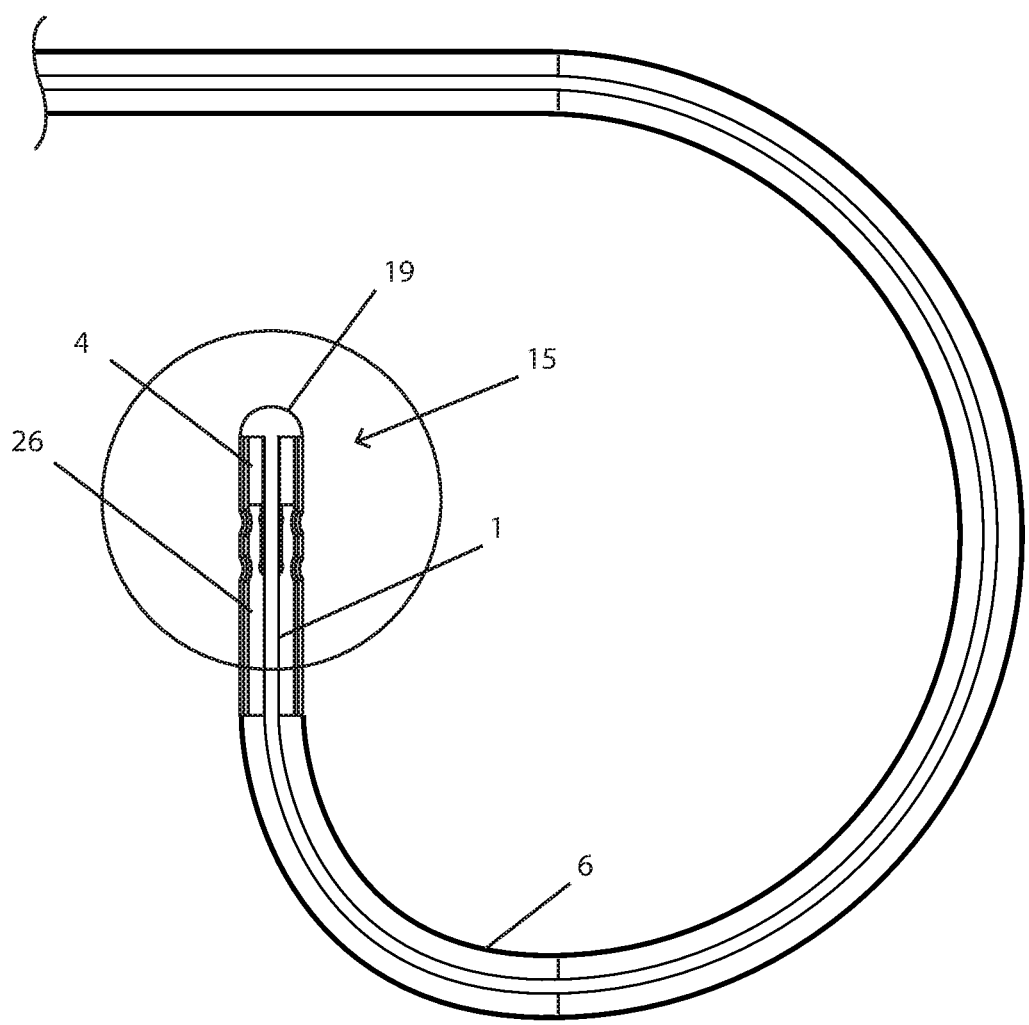
FIG. 24 is a cross-sectional view of a curved embodiment with a support spine.

In certain embodiments of the method, the medical device, dilator, and sheath are introduced into the heart via the inferior vena cava (as shown in FIGS. 23A and 23B). In alternative embodiments, the heart is accessed from the superior vena cava. Further details regarding superior and inferior approaches to the heart are be found in U.S. patent application Ser. No. 13/113,326 (filed on May 23, 2011), and Ser. No. 11/265,304 (filed on Nov. 3, 2005) both of which are incorporated herein by reference in their entirety.

In accordance with the method, for certain embodiments, the medical device comprises an elongate member having a distal region capable of adopting a curved shape to define a curved portion 30. For example, a support spine with a bias towards a curved shape may be positioned within a distal portion of a lumen of the elongate member, as described herein above. When the medical device tip advances through the material, the pre-shaped support spine causes the distal region to adopt a curved shape to direct the functional tip in a desired direction. In some embodiments, the curved portion 30 is defined by a radial arc and the energy delivery device 15 is directed away from cardiac structures, as shown in FIG. 23B, in order to decrease the risk of unwanted injury. As a further example, the distal region is adapted to form a 270 degree curve.

In alternative applications of a method of the present invention, medical device 20 may be used to create a channel through an occluded or stenosed lumen, or through other material within the body. Examples include blood vessels, stent-graft fenestrations, bile duct, or airways of the respiratory tract. In such embodiments, medical device 20 is positioned such that the electrode is adjacent to the material to be punctured. Energy is delivered from a source, such as a generator, via elongate member 6, to the target site such that a void, puncture, or channel is created in or through the tissue. Further details regarding delivery of energy to create channels through occlusions or other material is found in U.S. patent application Ser. No. 12/926,292, filed on Nov. 8, 2010, U.S. patent application Ser. No. 13/286,041, filed on Oct. 31, 2011, and U.S. Pat. No. 8,048,071, issued Nov. 1, 2011, all of which are incorporated herein by reference.

Thus, embodiments of the disclosure include a medical device comprising a flexible elongate member that defines a lumen, and a support spine affixed to the distal end and extending proximally therefrom within the elongate member lumen. In typical embodiments the support spine is not attached to a lumen surface or embedded in the elongate member's sidewall. In some embodiments, the support wire is configured to support at least a portion of the elongate member. Some embodiments of the medical device provide for distal end fluid delivery by defining apertures at or near the distal end that enable fluid communication between the lumen and the outside environment. Furthermore, in some such embodiments, the support spine extends from the distal end within a distal portion of the lumen such that a proximal portion of the lumen is substantially unobstructed by the support spine, thereby minimizing effects on fluid flow, at least within the proximal portion of the lumen.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A medical device for puncturing tissue comprising:
    an elongate member comprising a proximal region and a distal region, wherein the distal region comprises a flexible portion which is more flexible than the proximal region;
    the elongate member having a tubular configuration and including a metallic layer which is electrically conductive;
    a rigid energy delivery device at a distal end of the elongate member which is electrically connected to the metallic layer of the elongate member, the rigid energy delivery device being configured to deliver electrical energy to tissue when electrical energy is supplied to the rigid energy delivery device through the metallic layer;
    the flexible portion including at least one gap in a sidewall of the elongate member wherein the at least one gap comprises at least one cut in the sidewall;
    the elongate member defining a lumen and the distal region comprising a support spine in the lumen extending proximally from the distal end of the medical device along a length of the distal region; and
    wherein a proximal end of the support spine is independent of the sidewall of the elongate member and is unconstrained within the lumen whereby the support spine is operable during bending of the distal region to press against a tensile side of the distal region to provide support to the tensile side such that the support spine distributes stress along the distal region.

2. The medical device of claim 1, wherein the proximal region and energy delivery device are more rigid than the distal region.

3. The medical device of claim 1, wherein the rigid energy delivery device comprises a conductive dome, a conductive spacer which is proximal of the conductive dome and which defines a bore, and the support spine extending within the lumen proximally from the bore, wherein the conductive dome, the conductive spacer, and the support spine are joined together distal of the lumen.

4. The medical device of claim 1, wherein the distal region conforms to a tube or vasculature when the distal region is inserted or advanced through the tube or vasculature.

5. The medical device of claim 1, wherein the at least one gap of the distal region is partially blocked by the support spine.

6. The medical device of claim 1, wherein the support spine provides support to the distal region of the medical device.

7. The medical device of claim 1, wherein the distal region is configured to form a curve whereby it curves away from a central axis of the proximal region.

8. The medical device of claim 1, wherein the lumen extends from the proximal region to the distal end of the elongate member.

9. The medical device of claim 1, wherein the elongate member is configured such that energy is delivered along its length to the rigid energy delivery device.

10. The medical device of claim 1, wherein the support spine is comprised of electrically conductive material.

11. The medical device of claim 1, wherein the at least one cut is in a shape of a C-cut.

12. The medical device of claim 1, wherein the at least one cut is in a shape of a spiral shaped cut.

13. The medical device of claim 1, wherein the at least one cut is in a shape of an interrupted spiral shaped cut.

14. The medical device of claim 1, wherein the flexible portion includes at least one additional cut to thereby comprise interlocking cuts.

15. A method using the medical device of claim 1, wherein the method comprises:
- introducing the medical device into a body of a patient by inserting the medical device into a dilator and sheath, wherein the distal region of the medical device is sufficiently flexible to conform to a shape of the dilator and sheath;
- advancing the medical device in the dilator and sheath such that a distal tip of the medical device protrudes from the dilator and sheath while the distal region is positioned insides the dilator and sheath;
- positioning the distal tip of the medical device at a desired location in the body of the patient; and,
- delivering energy through the rigid energy delivery device at the distal tip to a tissue to create a puncture at a desired location in the body of the patient.

\* \* \* \* \*